United States Patent
Zlotkin et al.

(10) Patent No.: US 9,737,571 B2
(45) Date of Patent: Aug. 22, 2017

(54) COMPOSITIONS OF AQUATIC ORIGIN FOR PREVENTION OF CELL ADHESION AND METHODS OF USING SAME

(75) Inventors: Amir Zlotkin, Tel-Aviv (IL); Eliahu Zlotkin, Mevasseret Zion (IL); Amir Zlotkin, legal representative, Tel-Aviv (IL)

(73) Assignee: TEL HASHOMER MEDICAL RESEARCH INFRASTRUCTURE AND SERVICES LTD., Tel Hashomer (IL)

( * ) Notice: Subject to any disclaimer, the term of this patent is extended or adjusted under 35 U.S.C. 154(b) by 229 days.

(21) Appl. No.: 12/679,047

(22) PCT Filed: Sep. 21, 2008

(86) PCT No.: PCT/IL2008/001264
§ 371 (c)(1),
(2), (4) Date: Mar. 19, 2010

(87) PCT Pub. No.: WO2009/037714
PCT Pub. Date: Mar. 26, 2009

(65) Prior Publication Data
US 2011/0119774 A1    May 19, 2011

Related U.S. Application Data

(60) Provisional application No. 60/960,214, filed on Sep. 20, 2007.

(51) Int. Cl.
*A61K 35/60* (2006.01)
(52) U.S. Cl.
CPC .................................. *A61K 35/60* (2013.01)
(58) Field of Classification Search
CPC ....................................................... A61K 35/12
See application file for complete search history.

(56) References Cited

U.S. PATENT DOCUMENTS

| | | | |
|---|---|---|---|
| 3,697,285 A | 10/1972 | Faith et al. | |
| 5,410,023 A * | 4/1995 | Burzio | 530/329 |
| 2007/0003588 A1 | 1/2007 | Chinn et al. | |
| 2007/0020309 A1 | 1/2007 | Alberte et al. | |
| 2007/0098745 A1 | 5/2007 | Bruno | |

FOREIGN PATENT DOCUMENTS

| | | | |
|---|---|---|---|
| CN | 1096426 A | | 12/1994 |
| CN | 101072577 A | | 11/2007 |
| JP | 05004903 A | * | 1/1993 |
| JP | 05156088 A | * | 6/1993 |
| JP | 08193097 A | * | 7/1996 |
| JP | 2006016313 A | | 1/2006 |
| WO | WO 0218500 A1 | * | 3/2002 |
| WO | WO 03/092382 A1 | | 11/2003 |
| WO | WO 2005/109960 A2 | | 11/2005 |

OTHER PUBLICATIONS

Hellio et al. "Inhibitory Effects of Mediterranean Sponge Extracts and Metabolites on Larval Settlement of the Barnacle Balanus amphitrite". Marine Biotechnology. vol. 7 (Jun. 30, 2005) 297-305.*
Burgess et al. Biofouling, 2003 vol. 19 (Supplement), pp. 197-205.*
Bhosale et al. Mar. Biotechnol. vol. 4, (2002) 111-118.*
Search Report received in the related European Patent Application No. 08808065, dated Jul. 19, 2013.
Anderluh, et al., "N-Terminal truncation mutagenesis of equinatoxin II, a poreforming protein from the sea anemone Actinia equina", Protein Engineering, vol. 10, No. 7, 1997, pp. 751-755.
Cuypers, et al., "Jellyfish and other cnidarian envenomations cause pain by affecting TRPV1 channels", FEBS Letters, vol. 580, No. 24, 2006, pp. 5728-5732.
Groll, et al., "Novel surface coatings modulating eukaryotic cell adhesion and preventing implant infection", International Journal of Artificial Organs, vol. 32, No. 9, 2009, pp. 655-662.
Japanese Office Action, dated Jan. 9, 2013, received in the related Japanese Application No. 2010-525496.
Bernbom, et al., "Bacterial adhesion to stainless steel is reduced by aqueous fish extract coatings", Biofilms, 2006, vol. 3, No. 1, pp. 25-36.
The Journal of Japanese Association for Dental Science, 2006, vol. 25, pp. 82-86.
Macek, Peter., "Polypeptide cytolytic toxins from sea anemones (Actiniaria)", FEMS Microbiology Immunology, 1992, vol. 105, pp. 121-129.
Collection of Overviews of Lectures at the Meeting of Japan Society Bioscience, Biotechnology and Agrochemistry, 2006.
Anonymous: "Bacteria and antibacterial drugs" In: "The Merck Manual of Diagnosis and Therapy, 18th Edition", 2006, Merck Research Laboratories, Whitehouse Station, NJ pp. 1406-1440.
Appeal Decision in Japan 2010-525496, mailed Sep. 17, 2014, with translation.
Bonev, Boyan et al., "Effects of the Eukaryotic Pore-Forming Cytolysin Equinatoxin II on Lipid Membranes and the Role of Sphingomyelin," Biophysical J., 2003, vol. 84, pp. 2382-2392.
Examination Report in Singapore Application No. 201001864-6 mailed Oct. 24, 2013.
Ji, Yuantang et al., "The Application of Polyps Regeneration Experiment in Medical Research to Detect the Teratogenicity of Chemical Rapidly." Journal of Biology, Mar. 13, 1996, vol. 3, pp. 13-15.
Lie, Xingjie et al., "Comparison of Alkaline Extraction of Glycosaminoglycans from Four Marine Invertebrates," Journal of Yantai University (Natural Science and Engineering), Oct. 31, 2001, vol. 14, No. 4, pp. 264-268, including Abstract.

(Continued)

*Primary Examiner* — Amy L Clark
(74) *Attorney, Agent, or Firm* — Foley & Lardner LLP

(57) ABSTRACT

A composition comprising an extract from an aquatic organism is disclosed. The composition is capable of preventing adhesion of a cell to a surface and is devoid of cytotoxic or cytostatic activity. Medical devices comprising same and methods for preventing or treating a pathological infection using same are also disclosed.

1 Claim, 14 Drawing Sheets

(56) References Cited

OTHER PUBLICATIONS

Ma, Yuexin et al., "Antibacterial activities of epiphytic bacteria from the surface of seaweeds and invertebrates against fouling bacteria isolated from a netcage in coastal sea in Dalian," Journal of Dalian Fisheries University, Feb. 28, 2007, vol. 22, No. 1, pp. 11-15, including Abstract.
Office Action in China Application No. 200880112525.7, mailed Jul. 1, 2014, with translation.
Pungercar, Joze et al., "Sequence Analysis of the cDNA Encoding the Precursor of Equinatoxin V, a Newly Discovered Hemolysin from Sea Anemone Actinia Equina," Bioehimica et Biophysics Acta, 1997, vol. 1341, No. 2, pp. 105-107.
Search Report received in European Application No. 08808065.0, mailed Jun. 6, 2014.
Sher, et al., "Toxic polypeptides of the hydra-a bioinformatic approach to cnidarian allomones", Toxicon, vol. 45, pp. 865-879, (2005).
Sten, et al., "Cross-reactivity to eel, ellpout and ocean pout in codfish-allergic patient", Allergy, vol. 59, pp. 1173-1180, (2004).
Wang, Jinduan et al., "Purification and Amino Acid Composition Analysis of Cardiotonic Polypeptides from Qingdao Coast Sea Anemone," Journal of Fudan University (Natural Science), Dec. 31, 1996, vol. 35, No. 6, pp. 656-657, including Abstract.
Yu, Jie et al., "Study on Preparation and Application of Hydrolyzed Eel Head Protein by Enzymatic Methods," Chinese Journal of Marine Drugs, Oct. 31, 2000, vol. 5, pp. 50-54, including Abstract.
Chinese Office Action issued in co-pending Chinese Application No. 200880112525.7 mailed Feb. 10, 2015, with English translation.
Decision to Refuse a Patent issued in co-pending Korean Application No. 10-2014-7011383 dated Apr. 24, 2015, with partial English translation.
Vejborg, R. M., et al.; *Blocking of Bacterial Biofilm Formation by a Fish Protein Coating*; Applied and Environmental Microbiology, Jun. 2008; pp. 3551-3558.
Vejborg, R.M., et al.; *Anti-adhesive properties of fish tropomyosins*; Journal of Applied Microbiology, vol. 105, No. 1; 2008; pp. 141-150.
Intellectual Property Office of Singapore; Search Report and Written Opinion on application 2013066063 dated Nov. 30, 2015; 14 pages.

\* cited by examiner

COMPOSITIONS OF AQUATIC ORIGIN FOR PREVENTION OF CELL ADHESION AND METHODS OF USING SAME

SEQUENCE LISTING

The instant application contains a Sequence Listing which has been submitted via EFS-Web and is hereby incorporated by reference in its entirety. Said ASCII copy, created on Mar. 29, 2010, is named 09638201.txt and is 2,281 bytes in size.

FIELD AND BACKGROUND OF THE INVENTION

The present invention relates to extracts of aquatic organisms, and, more particularly, to the use of same for the prevention of cell adhesion.

Microorganisms can live and proliferate as individual cells swimming freely in the environment (as plankton), or they can grow as highly organized, multicellular communities encased in a self-produced polymeric matrix in close association with surfaces and interfaces. The latter microbial lifestyle is referred to as biofilms. Biofilm formation represents an ancient, protected mode of growth that allows microbial survival in hostile environments and allows microorganisms to disperse and colonize new niches [Hall-Stoodley et al., Nat Rev Microbiol. (2004) 2(2):95-108].

The composition of biofilms is complex and variable among different microbial species and even within the same species under different environmental conditions. Nonetheless, biofilm formation represents the normal lifestyle of microorganisms in the environment, and all microbes can make biofilms. Previous studies revealed that bacterial biofilm formation progresses through multiple developmental stages differing in protein profiles [Sauer et al., J Bacteriol. (2002) 184(4):1140-54], beginning with attachment to a surface, followed by immigration and division to form microcolonies, and finally maturation, involving expression of matrix polymers. Bacteria within each biofilm stage display phenotypes and possess properties that are markedly different from those of the same group growing planktonically [Sauer et al., J Bacteriol. (2004) 186(21):7312-26].

Biofilms are a major cause of systemic infections (e.g., nosocomial infections) in humans. In the body, biofilms can be associated with tissues (e.g., inner ears, teeth, gums, lungs, heart valves and the urogenital tract). An estimated 65% of bacterial infections in humans are biofilm in nature. Additionally, after forming biofilms, microorganisms tend to change their characteristics, sometimes drastically, such that doses of antibiotics which normally kill the organisms in suspended cultures are completely ineffective against the same microorganisms when the organisms are in attached or conglomerate biofilm form (U.S. Pat. No. 7,189,351).

One of the principal concerns with respect to products that are introduced into the body (e.g., contact lenses, central venous catheters, mechanical heart valves and pacemakers) or provide a pathway into the body is microbial infection and invariably biofilm formation. As these infections are difficult to treat with antibiotics, removal of the device is often necessitated, which is traumatic to the patient and increases the medical cost. Accordingly, for such medical apparatuses, the art has long sought means and methods of rendering those medical apparatuses and devices antimicrobial.

Previous reports have shown that in the marine environment, many soft bodied marine invertebrates such as sponges [Amade et al., Mar. Biol. (1987) 94: 271-275; Wilsanand et al., Ind. J. Mar. Sci (1999) 28:274-279], ascidians [Wahl et al., Mar. Ecol. Prog. Ser (1994) 110:45-57], and soft corals [Aceret et al., Comp. Biochem. Phys (1998) 120:121-126; Kelman et al., Mar. Ecol. Ser (1998) 169:87-95], produce secondary metabolites that exhibit antibacterial and antifungal activities [Harder et al., FEMS Microbiology Ecology (2003) 43(3):337-347]. Additionally, sea anemones (e.g., *Actinia equina*) have been shown to produce toxic, pore forming peptides belonging to the actinoporin family, termed equinatoxins [Kristan et al., J Biol. Chem. (2004) 279(45):46509-17]. Equinatoxins (i.e., equinatoxin 1, 2 and 3), have been purified by acetone precipitation, Sephadex G-50, CM-cellulose and CM-Sephadex column chromatography from the tentacles and bodies of the sea anemone *Actinia equine* [Macek P and Lebez D., Toxicon. (1988) 26(5):441-51]. These toxic proteins lyse and kill eukaryotic cells by forming toroidal protein-lipid pores in target cell membranes similarly to other small antimicrobial peptides [Anderluh et al., J. Biol. Chem. (2003) 278(46):45216-45223].

Since marine-aquatic plants and animals are continuously exposed to a large diversity and abundance of potentially harmful microorganisms in the form of biofilm, and it is known that marine life produce anti-microbial peptides, it is possible that broad spectrum natural factors that interfere with biofilm formation may also be present in marine life.

U.S. Publication No. 20070098745 discloses means of preventing biofilm formation by the use of reef fish microflora. This invention describes anti-biofilm substances derived from bacteria isolated from the epithelial mucosal surfaces of healthy coral reef fish (e.g., *Sparisoma ninidae* and *Lutjanus purpureus*). The bacterial isolates produce signals or toxins that prevent biofilm formation.

Due to the preponderance of biofilms and their deleterious effects, there remains a widely recognized need for, and it would be highly advantageous to identify novel anti-biofilm agents.

SUMMARY OF THE INVENTION

According to one aspect, there is provided a composition comprising an active agent from an aquatic organism, wherein said composition prevents or reduces adhesion of an organism to a surface and being devoid of cytotoxic or cytostatic activity.

According to further features in embodiments of the invention described below the active agent comprises a substantially whole aquatic organism.

According to still further features in the described embodiments the active agent comprises a homogenate of an aquatic organism.

According to still further features in the described embodiments the active agent comprises an isolated extract derived from an aquatic organism.

According to still further features, the isolated extract comprises a crude extract.

According to still further features in the described embodiments the isolated extract comprises a polar extract.

According to still further features in the described embodiments a polar solvent of the polar extract comprises acetonitrile.

According to still further features in the described embodiments active agent comprises at least one polypeptide.

According to still further features in the described embodiments the polypeptide is characterized by a peak mass selected from the group consisting of 19863 Da, 9926 Da, 8261 Da and 3655 Da.

According to still further features in the described embodiments the active agent comprises at least one polysaccharide.

According to still further features in the described embodiments the activity of the active agent is preserved following lyophilization.

According to still further features in the described embodiments the aquatic organism comprises a sessile organism.

According to still further features in the described embodiments the aquatic organism comprises a fish.

According to still further features in the described embodiments the fish is selected from the group consisting of eel and catfish.

According to still further features in the described embodiments the sessile organism comprises a sessile *Cnidarian*.

According to still further features in the described embodiments the sessile *Cnidarian* is selected from the group consisting of a coral, a sea anemone, a sea pen, an aquatic larva, a tube-dwelling anemone and a hydroid.

According to still further features in the described embodiments the sessile *Cnidarian* comprises a sea anemone.

According to still further features in the described embodiments the sea anemone comprises an *Actinia equine*.

According to still further features in the described embodiments the sea anemone comprises an *Aiptasia pulchella*.

According to still further features in the described embodiments the sessile *Cnidarian* comprises a hydroid.

According to still further features in the described embodiments the hydroid is selected from the group consisting of a *Chlorohydra viridissima* and a *Hydra vulgaris*.

According to still further features in the described embodiments the polar extract is from a tentacle tissue or an acrorhageal tissue of a sea anemone.

According to still further features in the described embodiments the sea anemone is an *Actinia equine*.

According to still further features in the described embodiments the polar extract from the *Actinia equine* comprises acetonitrile in the range of from about 1 to about 10% (v/v) of the total composition.

According to still further features in the described embodiments the polar extract from the *Actinia equine* comprises acetonitrile in the range of from about 40 to about 60% (v/v) of the total composition.

According to still further features in the described embodiments the polar extract from the *Actinia equine* comprises acetonitrile in the range of from about 40 to about 60% (v/v) of the total composition.

According to still further features in the described embodiments the polar extract is from an *Aiptasia pulchella*.

According to still further features in the described embodiments the polar extract from the *Aiptasia pulchella* is selected from the group consisting of about 8-12% acetonitrile, about 16-20% acetonitrile, about 22-26% acetonitrile and about 26-30% acetonitrile.

According to still further features in the described embodiments the organism is a single cell organism.

According to still further features in the described embodiments the composition is further capable of inhibiting aggregation of cells.

According to still further features in the described embodiments the single cell organism is comprised in a biofilm.

According to still further features in the described embodiments the single cell organism is selected from the group consisting of a bacteria, a fungus, a protozoan and an archaea.

According to still further features in the described embodiments the fungi comprises a yeast.

According to still further features in the described embodiments the surface is selected from the group consisting of a fabric, a fiber, a foam, a film, a concrete, a masonry, a glass, a metal and a plastic.

According to still further features in the described embodiments the surface comprises a biological tissue.

According to still further features in the described embodiments the biological tissue comprises a mammalian tissue.

According to still further features in the described embodiments the mammalian tissue comprises a skin.

According to still further features in the described embodiments a formulation of the composition of matter is selected from the group consisting of a spray, a gel, a paint and a cream.

According to another aspect, there is provided a method of preventing adhesion of a single cell organism to a surface, the method comprising contacting the single cell organism with a composition comprising an active agent from an aquatic organism capable of preventing adhesion of the single cell organism to the.

According to still further features in the described embodiments the active agent is devoid of cytotoxic or cytostatic activity.

According to still further features in the described embodiments the active agent comprises a crude extract.

According to still further features in the described embodiments the active agent comprises a polar extract.

According to still further features in the described embodiments the active agent comprises a substantially whole aquatic organism.

According to still further features in the described embodiments the polar extract comprises at least one isolated polypeptide.

According to still further features in the described embodiments the isolated polypeptide comprises equinatoxin.

According to still further features in the described embodiments the polar extract comprises at least one isolated polysaccharide.

According to still further features in the described embodiments the preventing adhesion of the organism is effected in vitro.

According to still further features in the described embodiments the preventing adhesion of the organism is effected ex vivo.

According to still further features in the described embodiments the preventing adhesion of the organism is effected in vivo.

According to still further features in the described embodiments the organism is a single cell organism.

According to still further features in the described embodiments the single cell organism is comprised in a biofilm.

According to still further features in the described embodiments the single cell organism is selected from the group consisting of a bacteria, a fungi, a protozoa and an archaea.

According to still further features in the described embodiments the fungi comprises a yeast.

According to still further features in the described embodiments the surface is selected from the group consisting of a fabric, a fiber, a foam, a film, a concrete, a masonry, a glass, a metal and a plastic.

According to still further features in the described embodiments the surface is a tissue.

According to still further features in the described embodiments the tissue comprises a mammalian tissue.

According to still further features in the described embodiments the mammalian tissue comprises a skin.

According to yet another aspect, there is provided a pharmaceutical composition comprising a pharmaceutically acceptable carrier or diluent and an active agent from an aquatic organism, being capable of preventing adhesion of a single cell organism to a surface.

According to still further features in the described embodiments the active agent is devoid of cytotoxic or cytostatic activity.

According to still further features in the described embodiments a formulation of the composition is selected from the group consisting of a spray, a cream and a gel.

According to still another aspect, there is provided a method of preventing or treating a pathogen infection in a subject in need thereof, the method comprising administering to the subject a therapeutically effective amount of the pharmaceutical composition, thereby treating or preventing the pathogen infection.

According to still further features in the described embodiments the treating is effected in vivo.

According to still further features in the described embodiments the treating is effected ex vivo.

According to still further features in the described embodiments a pathogenic organism of the pathogen infection is capable of growing in or on a biofilm.

According to still further features in the described embodiments the pathogen infection comprises a bacterial infection.

According to still further features in the described embodiments the bacterial infection comprises gram positive bacteria.

According to still further features in the described embodiments the gram positive bacteria is *Staphylococcus aureus*.

According to still further features in the described embodiments the bacterial infection comprises gram negative bacteria.

According to still further features in the described embodiments the gram negative bacteria is selected from the group consisting of *Acinetobacter baumannii*, *Pseudomonas aeruginosa* and *Escherichia coli*.

According to still further features in the described embodiments a pathogenic organism of the pathogen infection is antibiotic resistant.

According to still further features in the described embodiments the pathogen infection is selected from the group consisting of a fungal infection, a protozoa infection, a bacterial infection and an archaea infection.

According to an additional aspect, there is provided a method of identifying an anti-biofilm composition, the method comprising contacting a plurality of compositions from an aquatic organism with biofilm forming bacteria, assaying a biofilm activity of the biofilm forming bacteria in a presence of the plurality of compositions and identifying from the plurality of compositions at least one composition having the anti-biofilm activity above a predetermined threshold, thereby identifying the anti biofilm composition.

According to still further features in the described embodiments the aquatic organism comprises a sessile organism.

According to still further features in the described embodiments the aquatic organism comprises a fish.

According to still further features in the described embodiments the fish is selected from the group consisting of eel and catfish.

According to still further features in the described embodiments the sessile organism comprises a sessile *Cnidarian*.

According to still further features in the described embodiments the sessile *Cnidarian* is selected from the group consisting of a coral, a sea anemone, a sea pen, an aquatic larva, a tube dwelling anemone and a hydroid.

According to still further features in the described embodiments the sessile *Cnidarian* comprises a sea anemone.

According to still further features in the described embodiments the sea anemone comprises an *Actinia equine*.

According to still further features in the described embodiments the sea anemone comprises an *Aiptasia pulchella*.

According to still further features in the described embodiments the sessile *Cnidarian* comprises a hydroid.

According to still further features in the described embodiments the hydroid is selected from the group consisting of a *Chlorohydra viridissima* and a *Hydra vulgaris*.

According to still further features in the described embodiments the plurality of compositions of the aquatic organism comprises a crude extract.

According to still further features in the described embodiments the crude extract is from tentacle tissue.

According to still further features in the described embodiments the crude extract is from acrorhageal tissue.

According to still further features in the described embodiments the plurality of compositions of the aquatic organism comprises a polar extract.

According to still further features in the described embodiments the polar extract is from tentacle tissue.

According to still further features in the described embodiments the tentacle tissue is from *Actinia equine*.

According to still further features in the described embodiments the biofilm forming bacteria comprises gram positive bacteria.

According to still further features in the described embodiments the gram positive bacteria is *Staphylococcus aureus*.

According to still further features in the described embodiments the biofilm forming bacteria comprises gram negative bacteria.

According to still further features in the described embodiments the gram negative bacteria is selected from the group consisting of *Acinetobacter baumannii*, *Pseudomonas aeruginosa* and *Escherichia coli*.

According to yet an additional aspect, there is provided a medical device comprising any of the compositions described herein.

According to still further features in the described embodiments the medical device is an intracorporeal device.

According to still further features in the described embodiments the medical device is an extracorporeal device.

According to still further features in the described embodiments the composition is coated on a surface of the device.

According to still further features in the described embodiments the composition is incorporated into a polymeric matrix of the medical device.

According to yet an additional aspect, there is provided use of the compositions of the present invention to prevent cell adherence to an implantable medical device.

According to yet an additional aspect, there is provided use of the compositions of the present invention to prevent cell adherence to a medical instrument.

According to yet an additional aspect, there is provided a method of preventing or reducing biofilm formation or fouling of an underwater surface, the method comprising treating the water with any of the compositions described herein.

According to yet an additional aspect, there is provided a method of preventing or reducing biofilm formation or fouling of an underwater surface, the method comprising coating the surface with any of the compositions described herein The present invention successfully addresses the shortcomings of the presently known adhesion and biofilm formation of single cell organisms by providing a composition of matter of sessile aquatic organisms. Furthermore, the present invention provides for a pharmaceutical composition, a method for identifying anti-biofilm compositions and a method for preventing or treating pathological infection as well as a medical device comprising an anti-biofilm composition from an aquatic organism attached thereto.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

The term "active agent" refers to any agent derived from an aquatic organism having an anti-adhesive effect, including a whole, living organism; a part thereof, homogenate or extract thereof, including a crude extract or a polar extract.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A shows a general view, with acrorhagi (territorial aggression organs) extended. The size is about 5-6 cm in height. FIG. 1B is a schematic drawing of *Actinia* with the various organs highlighted.

FIGS. 3A and 3B show chromatographic separations of acrorhagi (FIG. 3A) and tentacle (FIG. 3B) tissues extract on a RP-HPLC C-8 column. The elution pattern was monitored at 215 nm. FIG. 3C shows anti-adhesive effect of selected tentacular fractions on *Acinetobacter baumannii*, with PBS serving as a positive control. Fractions obtained from the chromatographic separation of *Actinia tentacular* tissue—and their anti-adhesion effect, each fraction was diluted 1:50. Of note, the most active fractions (less than 20% adhesion) from the tentacle separation (13-14, 17-20, 45-46) are marked by a red circle (see FIG. 3B), and were chosen for further characterization. Similar effects were obtained by the marked (arrows) acrorhageal fractions (see FIG. 3A, data not shown). FIG. 3D shows gel electrophoresis of proteins in selected fractions. Active fractions were separated on a 15% denaturing SDS-PAGE gel followed by silver staining (as explained in detail in example 2). While fractions 45 and 46 revealed many protein bands, the other fractions revealed almost exclusively a pair of proteins with a molecular weight of around 60 kDa. Of note, peptides shorter than approximately 8 kDa could not be observed.

FIG. 6A shows a high-throughput polystyrene microplate assay. S. aureus (ATCC 25923) was grown in 96-well round-bottom polystyrene plates (as described in detail in Example 3) and stained with crystal violet solution. For quantification of attached cells, crystal violet solution left in the wells was solubilized in 250 µl of 1% SDS, and the optical density read at 595 nm. The anti-adherence effect of crude material of A. equina tentacles was checked with 3 dilutions 1:10, 1:100 and 1:1000, in triplicate compared to positive control (bacteria incubated with PBS). The result (bottom panel of FIG. 6A) is based on spectrometric measurement. FIG. 6B shows a qualitative observation. S. aureus (ATCC 25923) was grown in 2 ml medium in 5 ml polystyrene tubes and stained with crystal violet solution (as further described in Example 3). Of note, decrease in attached bacteria due to addition of crude material in different dilutions can be observed. FIG. 6C depicts a fluorescent microscopic assay for biofilm formation on glass slides. E. coli (DH5-α strain U85) containing plasmids for the expression of Green Fluorescent Protein (GFP) were plated on a glass cover slide with A. equina tentacle extract, two chromatographic fractions (14, 17) from this extract, or recombinant equinatoxin. Adhered bacteria were visualized after 1, 7 and 22 hours with inverted epi-flouresent IX2-81 microscope (Olympus, USA). Of note, incubation of the bacteria with A. equina tentacle extract, two chromatographic fractions (14, 17) from this extract, or recombinant equinatoxin, results in an ablation of bacterial adherence. These results indicate that prevention of biofilm formation occurs at the initial stages of the attachment.

FIG. 7A shows the active material previously obtained (in FIG. 3) by RP-HPLC (T-18) which was rechromatographed on the same column and peaks were collected. Active peak 75 (red arrow) was measured by MALDI-TOF using sinapinic acid as a matrix. FIG. 7B demonstrates the resulted spectra existent of several peaks at masses of 19863, 9926, 8261, 3655 Da, presumably proteins. Of note, these data reveal the ability to isolate and chemically characterize the relevant substances. The activity of equinatoxin (Eq) is noteworthy.

FIGS. 11A and 11B show HPLC analysis of fractions 2 and 3 wherein the different peaks are numbered; FIG. 11C shows Dextran ladder—mean ladder of Glucose oligomers. Of note, the main peak in both FIGS. 11A and 11B (peak number 1) represents a di-glucose (marked by circle).

DESCRIPTION OF THE PREFERRED EMBODIMENTS

The present invention is of compositions extracted from aquatic organisms for prevention of cell adhesion and methods of using same.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

One of the major concerns in medicine is microbial biofilm formation. In humans, biofilms are a cause of systemic infections (e.g., nosocomial infections) and are a major concern when introducing products into the body (e.g., contact lenses, central venous catheters, mechanical heart valves and pacemakers). Biofilms are also a problem in many industries including the food, pharmaceutical, paint, water, shipping and engineering industries causing, amongst a wide range of negative effects, accelerated corrosion in industrial systems, oil souring and biofouling. Biofilms are very difficult to eliminate since microbes growing within are highly organized and can withstand hostile environments, such as high temperatures and anti-microbial agents (e.g., antibiotics).

It has been previously reported that marine organisms (e.g. sponges) produce secondary metabolites that exhibit antibacterial and antifungal activities [Amade et al., supra]. Moreover, sea anemones (e.g., Actinia equina) have been shown to produce toxic, pore forming peptides (i.e., equinatoxins), which lyse and kill eukaryotic cells similarly to other small antimicrobial peptides [Anderluh et al., supra].

Whilst reducing the present invention to practice, the present inventors discovered that aquatic sessile organisms comprise anti-biofilm properties.

Figure 2:
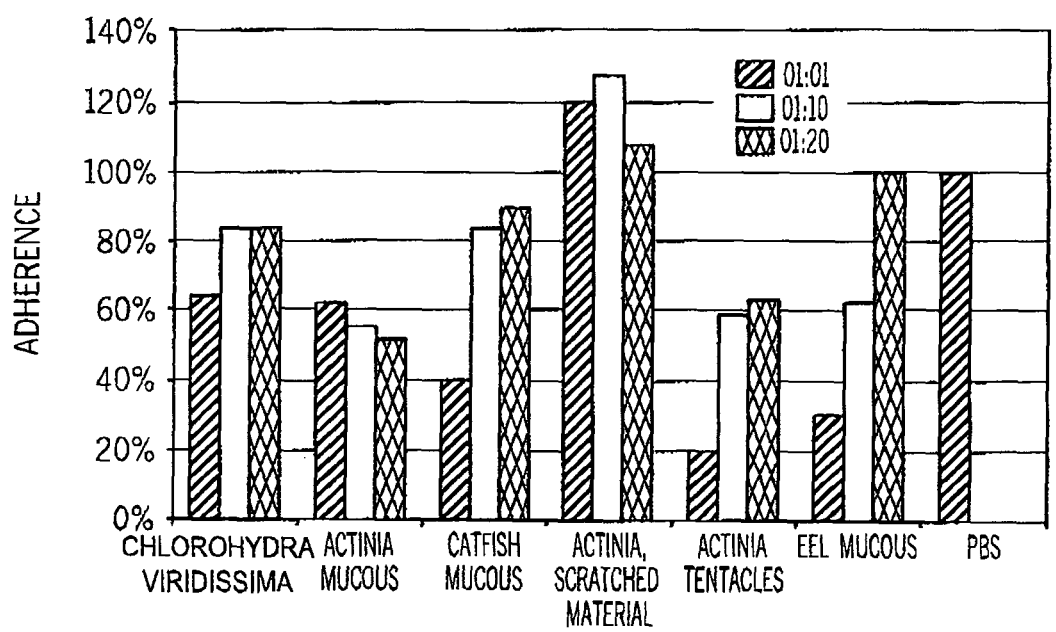
FIG. 2 is a graph depicting the anti-adhesive effect of crude extracts of fish and *cnidarians*. Samples derived from surface mucous collected from fish (eel, catfish) and homogenates of sessile *cnidarians* (two kinds of hydrae and sea anemones) were incubated with the virulent clinical bacterial strain *Acinetobacter baumannii* and the adhesion of the bacteria was tested using the crystal violet assay. Results are presented as percent of bacterial adhesion compared to 100% positive control, at three different sample dilutions (in PBS).
Figure 5:
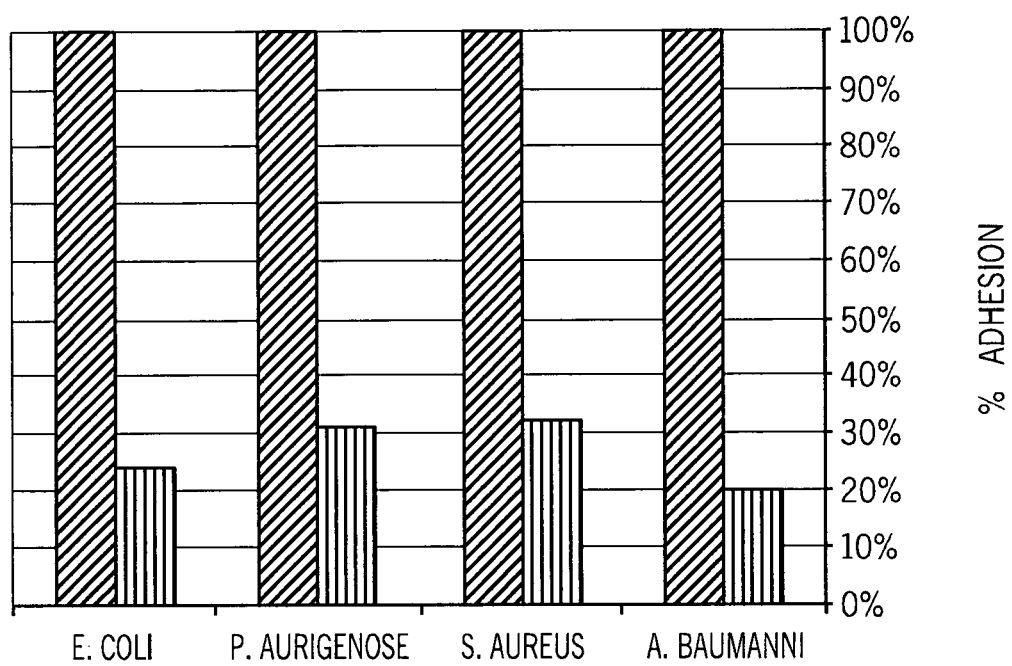
FIG. 5 is a bar graph depicting anti-adhesive activity of fraction 13 against different gram positive and gram negative bacteria. Microplate adhesion bioassay was performed on four clinical isolates of *Acinetobacter baumanni, Staphylococcus aureus, Pseudomonas aurigenose* and *E. coli*, using fraction 13 from tentacle separation at 1:100 dilution. Bacterial adhesion (blue) is expressed as percent of PBS control (100% adhesion, red). Of note, S. aureus is a gram-positive bacteria and the rest are gram-negative bacteria.
Figure 10:
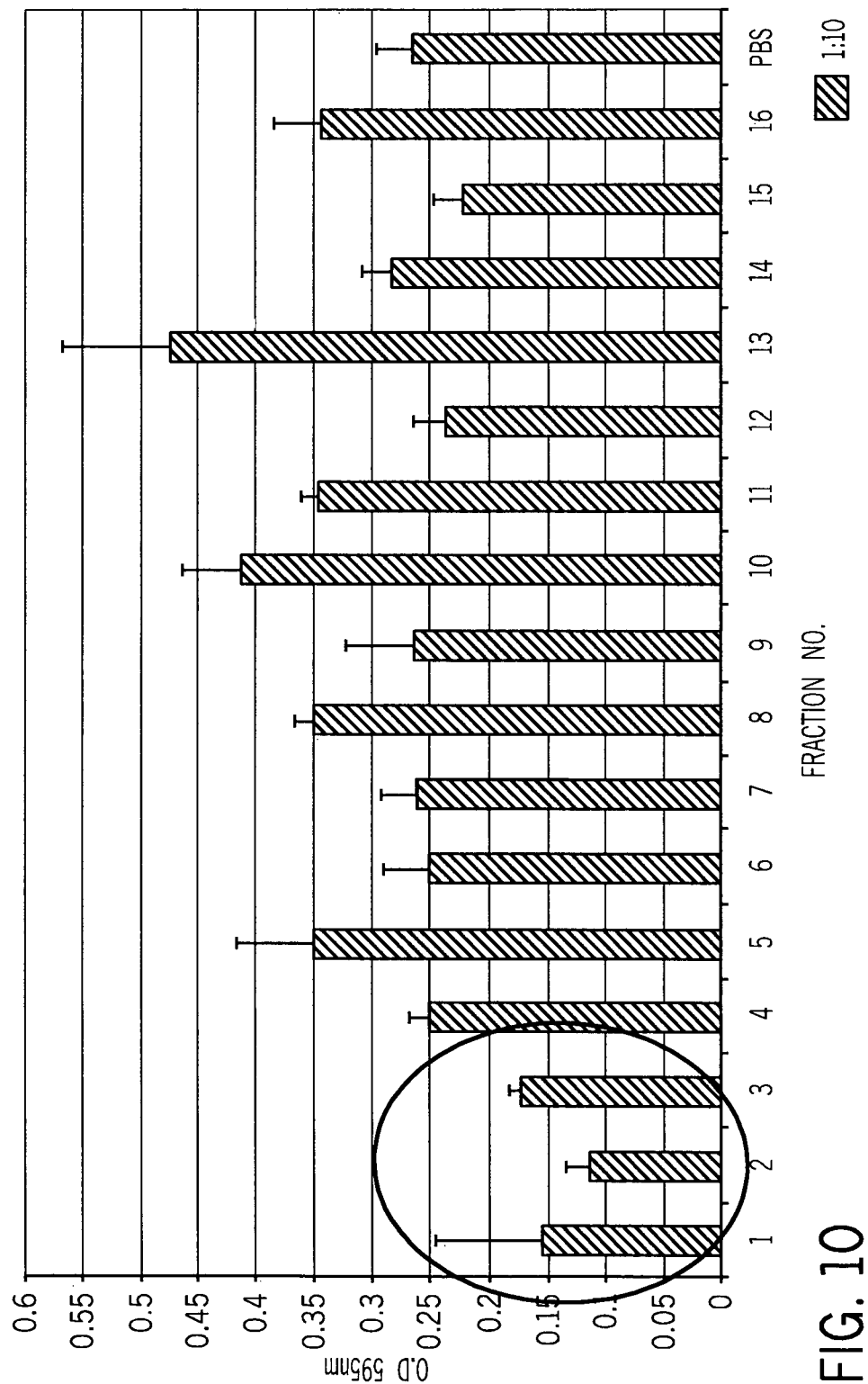
FIG. 10 is a bar graph depicting separation of the low molecular fraction from G-75 column using RP-HPLC with c-18 column. This separation resulted in several fractions including active fractions (fractions 2 and 3—marked by a red circle) which were identified as polysaccharides after MS analysis.
Figures 11A, 11B, 11C:
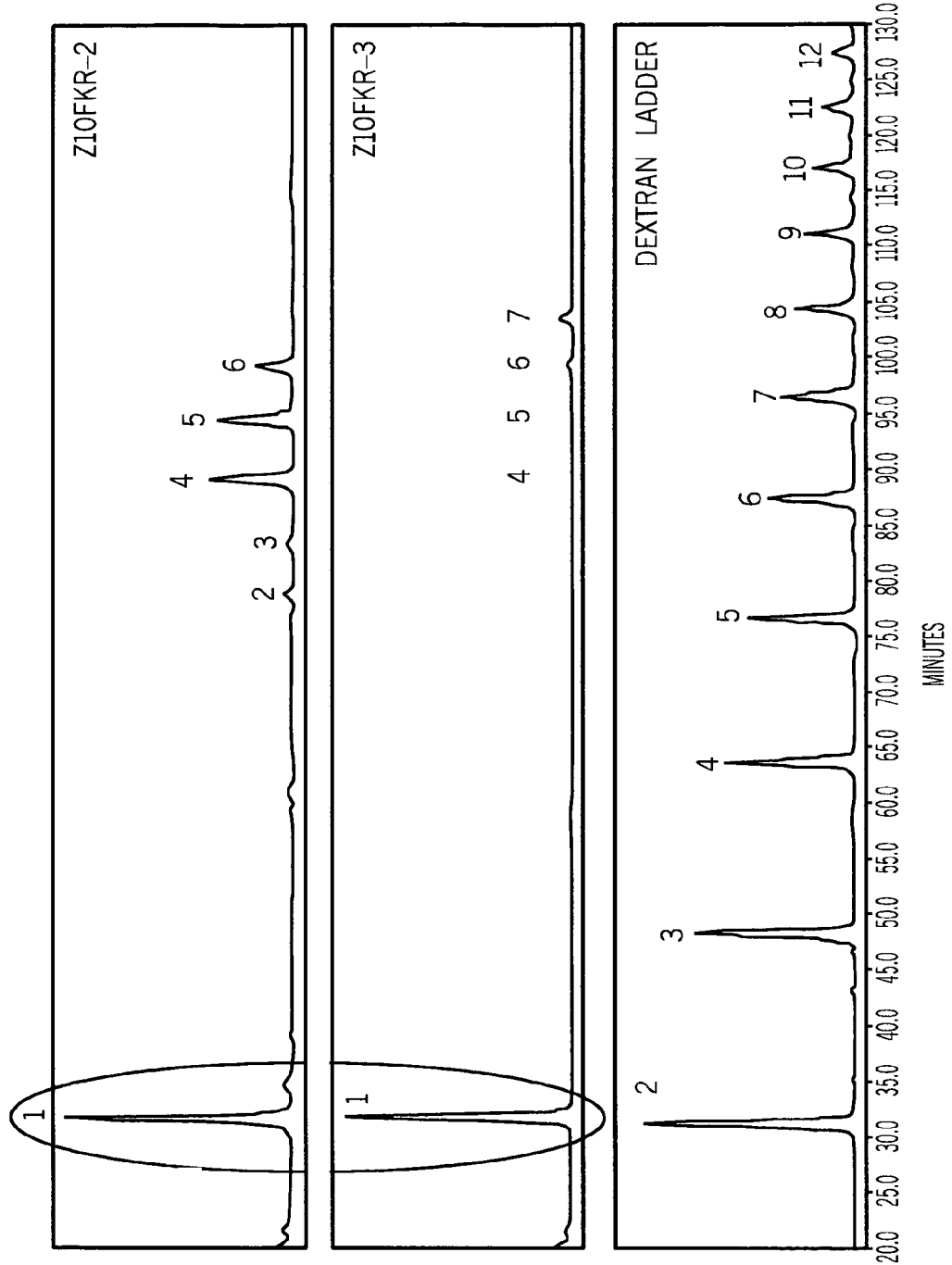
FIGS. 11A-C are figures depicting separation profiles of polysaccharide based on size.
Figure 12:
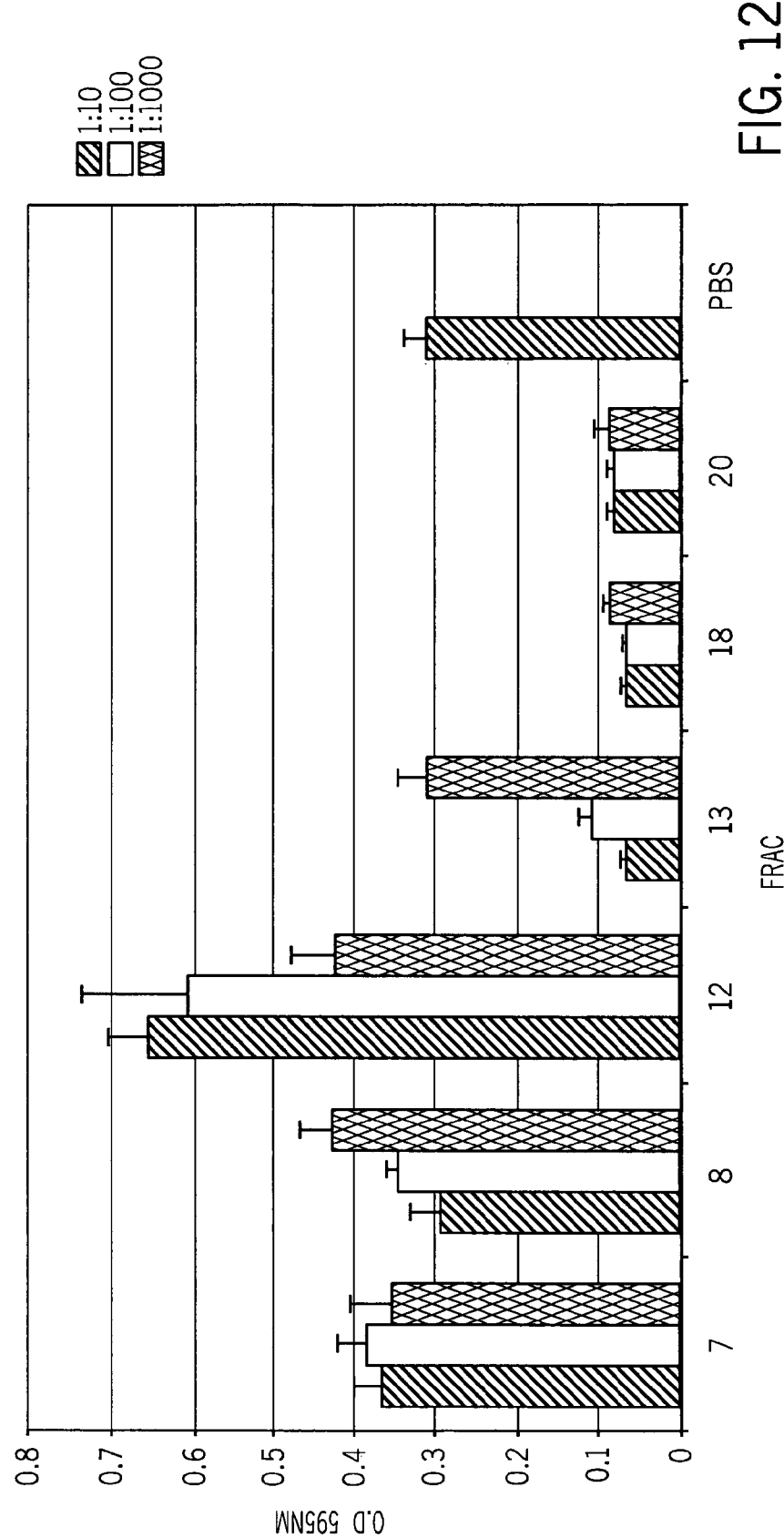
FIG. 12 is a figure depicting RP-HPLC separation of the high molecular fraction from G-75. The separation resulted in at least 3 fractions (13, 18 and 20) with high anti adherence activity. MS analysis and gel electrophoresis showed that the active fractions are peptides.

As is shown hereinbelow and in the Examples section which follows, the present inventors have shown that crude extracts of fish (eel, catfish) and sessile *cnidarians* (hydroids and sea anemones), extracted according to the teachings of the present invention, prevent bacterial adherence to surfaces (FIG. 2). These extracts were not bactericidal and did not affect bacterial growth (Table 1, Example 2, hereinbelow). A bacterial anti-adhesion effect was further substantiated for isolated fractions of *Actinia equina* tentacles as well as for *Actinia equina* acrorhageal tissue (FIGS. 3A-D). The anti-adhesion effect of isolated fractions was similarly effective on gram positive and gram negative bacteria (FIG. 5) inhibiting bacterial adhesion and consequently biofilm formation (FIG. 6C). The active agents in the *Actinia equina* fractions were identified as being polypeptides (FIG. 7B). Additionally, crude extracts of *Aiptasia pulchella* revealed anti-adherence/biofilm formation activity (FIG. 10). The active agents in the *Aiptasia pulchella* were identified as being polysaccharides and polypeptides (FIGS. 10-12).

The active protein from *Actinia equine* is equinatoxin 2-Equinatoxin-2 precursor (Equinatoxin II) (EqT II) (EqTII). Genbank ACCESSION no. P61914:

(SEQ ID NO: 1)
MSRLIIVFIVVTMICSATALPSKKIIDEDEEDEKRSADVAGAVIDGASLS

FDILKTVLEALGNVKRKIAVGVDNESGKTWTALNTYFRSGTSDIVLPHKV

PHGKALLYNGQKDRGPVATGAVGVLAYLMSDGNTLAVLFSVPYDYNWYSN

WWNVRIYKGKRRADQRMYEELYYNLSPFRGDNGWHTRNLGYGLKSRGFMN

SSGHAILEIHVSKA.

Taken together the present teachings portray a wide range of novel anti-adhesive agents derived from aquatic sessile organisms and in particular from sessile *Cnidarians*. The broad spectrum of the anti adhesion effects of these agents (e.g. inhibiting adhesion of gram positive and gram negative bacteria) together with their ability to effect the initial, vulnerable stages of microbial biofilm formation, makes these agents prime candidates as anti-biofilm agents. Moreover, the anti-adhesive agents described herein are clonable enabling modifications and mass production thereof In addition their stability (i.e. resistance to environmental conditions) makes these agents suitable for a diverse array of applications.

Thus, according to one aspect of the present invention there is provided a method of preventing adhesion of a cell to a surface, the method comprising contacting the cell with a composition of matter from an aquatic organism capable of preventing adhesion of the cell to a surface, thereby preventing adhesion of a cell to a surface.

Optionally, the cell may comprise a single cell organism. As used herein the phrase "single cell organism" refers to a unicellular organism also termed a microorganism or a microbe. The single cell organism of the present invention can be a eukaryotic single cell organism (e.g., protozoa or fungi for example yeast) or a prokaryotic single cell organism (e.g., bacteria or archaea). The single cell organisms of the present invention may be in any cellular environment, such as for example, in a biofilm, as isolated cells or as a cell suspension.

As used herein the term "biofilm" refers to an extracellular matrix in which microorganisms are dispersed and/or form colonies. The biofilm typically is made of polysaccharides and other macromolecules.

Exemplary bacterial cells, whose adhesion may be prevented according to the method of the present invention, include gram positive bacteria and gram negative bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis*, *Bifidobacterium* spp., *Clostridium botulinum*, *Clostridium perfringens*, *Clostridium* spp., *Clostridium tetani*, *Corynebacterium diphtheriae*, *Corynebacterium jeikeium*, *Enterococcus faecalis*, *Enterococcus faecium*, *Erysipelothrix rhusiopathiae*, *Eubacterium* spp., *Gardnerella vaginalis*, *Gemella morbillorum*, *Leuconostoc* spp., *Mycobacterium abscessus*, *Mycobacterium avium* complex, *Mycobacterium chelonae*, *Mycobacterium fortuitum*, *Mycobacterium haemophilium*, *Mycobacterium kansasii*, *Mycobacterium leprae*, *Mycobacterium marinum*, *Mycobacterium scrofulaceum*, *Mycobacterium smegmatis*, *Mycobacterium terrae*, *Mycobacterium tuberculosis*, *Mycobacterium ulcerans*, *Nocardia* spp., *Peptococcus niger*, *Peptostreptococcus* spp., *Proprionibacterium* spp., *Sarcina lutea*, *Staphylococcus aureus*, *Staphylococcus auricularis*, *Staphylococcus capitis*, *Staphylococcus cohnii*, *Staphylococcus epidermidis*, *Staphylococcus haemolyticus*, *Staphylococcus hominis*, *Staphylococcus lugdanensis*, *Staphylococcus saccharolyticus*, *Staphylococcus saprophyticus*, *Staphylococcus schleiferi*, *Staphylococcus similans*, *Staphylococcus warneri*, *Staphylococcus xylosus*, *Streptococcus agalactiae* (group B *streptococcus*), *Streptococcus anginosus*, *Streptococcus bovis*, *Streptococcus canis*, *Streptococcus equi*, *Streptococcus milleri*, *Streptococcus mitior*, *Streptococcus mutans*, *Streptococcus pneumoniae*, *Streptococcus pyogenes* (group A *streptococcus*), *Streptococcus salivarius*, *Streptococcus sanguis*.

The term "Gram-negative bacteria" as used herein refer to bacteria characterized by the presence of a double membrane surrounding each bacterial cell. Representative Gram-negative bacteria include *Acinetobacter calcoaceticus*, *Acinetobacter baumannii*, *Actinobacillus actinomycetemcomitans*, *Aeromonas hydrophila*, *Alcaligenes xylosoxidans*, *Bacteroides*, *Bacteroides fragilis*, *Bartonella bacilliformis*, *Bordetella* spp., *Borrelia burgdorferi*, *Branhamella catarrhalis*, *Brucella* spp., *Campylobacter* spp., *Chalmydia pneumoniae*, *Chlamydia psittaci*, *Chlamydia trachomatis*, *Chromobacterium violaceum*, *Citrobacter* spp., *Eikenella corrodens*, *Enterobacter aerogenes*, *Escherichia coli*, *Flavobacterium meningosepticum*, *Fusobacterium* spp., *Haemophilus influenzae*, *Haemophilus* spp., *Helicobacter pylori*, *Klebsiella pneumoniae*, *Klebsiella* spp., *Legionella* spp., *Leptospira* spp., *Moraxella catarrhalis*, *Morganella morganii*, *Mycoplasma pneumoniae*, *Neisseria gonorrhoeae*, *Neisseria meningitidis*, *Pasteurella multocida*, *Plesiomonas shigelloides*, *Prevotella* spp., *Proteus* spp., *Providencia rettgeri*, *Pseudomonas aeruginosa*, *Pseudomonas* spp., *Rickettsia prowazekii*, *Rickettsia rickettsii*, *Rochalimaea* spp., *Salmonella* spp., *Salmonella typhi*, *Serratia marcescens*, *Shigella* spp., *Shigella sonnei*, *Treponema carateum*, *Treponema pallidum*, *Treponema pallidum endemicum*, *Treponema pertenue*, *Veillonella* spp., *Vibrio cholerae*, *Vibrio vulnificus*, *Yersinia enterocolitica*, *Yersinia pestis*.

The term "fungi" as used herein refers to the heterotrophic organisms characterized by the presence of a chitinous cell wall, and in the majority of species, filamentous growth as multicellular hyphae. Representative fungi whose adhesion may be prevented according to the method of the present invention include *Candida albicans*, *Saccharomyces cerevisiae*, *Candida glabrata*, *Candida parapsilosis* and *Candida dubliniensis*.

As used herein the phrase "preventing adhesion" refers to reducing or eliminating cell attachment to a surface (e.g. by reducing the rate of growth on a surface). Preferably, the compositions of the present invention prevent cell adhesion by as much as 10%, more preferably by 20%, more preferably by 30%, more preferably by 40%, more preferably by 50%, more preferably by 60%, more preferably by 70%, more preferably by 80%, more preferably by 90% and most preferably by 100% as measured by a cell adhesion assay. Exemplary cell adhesion assays are described herein below and in the Examples section that follows. It will be appreciated that the compositions of the present invention may also be capable of preventing cell aggregation (i.e. cell aggregation not to a surface).

The present invention contemplates prevention of cellular adhesion to a wide variety of surfaces including fabrics, fibers, foams, films, concretes, masonries, glass, metals, plastics, polymers, and like.

According to one embodiment, the surface is comprised in a device that is susceptible to biofilm formation. Exemplary devices whose surfaces are contemplated by the present invention include, but are not limited to, vessel hulls, automobile surfaces, air plane surfaces, membranes, filters, and industrial equipment.

The surface may also be comprised in medical devices, instruments, and implants. Examples of such medical devices, instruments, and implants include any object that is capable of being implanted temporarily or permanently into a mammalian organism, such as a human. Representative medical devices, instruments, and implants that may be used according to the present invention include, for example, central venous catheters, urinary catheters, endotracheal tubes, mechanical heart valves, pacemakers, vascular grafts, stents and prosthetic joints. Methods of preventing cell attachment to medical devices and further examples thereof are described herein below.

According to another embodiment the surface is comprised in a biological tissue, such as for example, mammalian tissues e.g. the skin.

As mentioned, the method of the present invention is effected by contacting the cell with a composition from an aquatic organism capable of preventing adhesion of the cell to a surface.

As used herein the term "contacting" refers to the positioning of the compositions of the present invention such that they are in direct or indirect contact with the adhesive cells in such a way that the active agent comprised within is able to prevent adhesion of cells thereto. Thus, the present invention contemplates both applying the compositions of the present invention to a desirable surface and/or directly to the adhesive cells.

The contacting may be effected in vivo (i.e. within a mammalian body), ex vivo (i.e. in cells removed from the body) and/or in vitro (i.e. outside a mammalian body).

Contacting the compositions with a surface can be effected using any method known in the art including spraying, spreading, wetting, immersing, dipping, painting, ultrasonic welding, welding, bonding or adhering. The compositions of the present invention may be attached as monolayers or multiple layers.

According to one embodiment, the compositions of the present invention may be comprised in a whole living aquatic organism. For example, the present invention contemplates adding live aquatic organisms to an underwater environment such that they are able to contact a surface and/or cells adhered thereto (e.g. underwater pipes, ship hull) preventing microorganism adhesion thereto. It will be appreciated that the active agent may be secreted from the aquatic organism. In this case, the aquatic organism does not have to be in direct contact with the surface or microorganism cells, but in sufficient proximity such that the active agent is able to diffuse to its site of action. Thus, the compositions of the present invention may be secreted into water and used in water purification treatments such as for example desalination of sea water or brackish water.

As used herein the phrase "aquatic organism" refers to an organism living in a water environment (marine or freshwater) such as for example a fish or a sessile aquatic organism.

As used herein, the phrase "sessile aquatic organism" refers to an aquatic organism which is not freely moving for at least some a part of its life cycle. Aquatic sessile organisms are usually permanently attached to a solid substrate of some kind, such as to a rock or the hull of a ship due to physical anchorage to the substrate, or for any other reason (e.g. stone fish).

Exemplary sessile organisms include, but are not limited to, sessile *cnidarians* such as corals, sea anemones (e.g. *Actinia equine* and *Aiptasia pulchella*), sea pens, aquatic sessile larva (e.g., jellyfish larva), tube dwelling anemones and hydroids (e.g. *Chlorohydra viridissima* and *Hydra vulgaris*).

Exemplary fish that may be used according to this aspect of the present invention are preferably those dwelling in shallow waters or those that hide at the bottom layer of the ocean, sometimes in holes or caves. Such fish include eel and catfish.

According to another embodiment, the compositions of the present invention may be isolated from aquatic organisms.

As used herein, the term "isolated" refers to a composition that has been removed from its in-vivo location (e.g. aquatic organism). Preferably the isolated compositions of the present invention are substantially free from other substances (e.g., other proteins that do not comprise anti-adhesive effects) that are present in their in-vivo location (i.e. purified or semi-purified).

Thus, according to one embodiment of this aspect of the present invention, the compositions of the present invention can be crude extracts or polar extracts.

As used herein the phrase "crude extract" refers to an unprocessed extract of cells or tissues of aquatic organism origin. Methods of obtaining crude extracts are well known in the art and include collection of cells or tissues, dissection of cells or tissues and homogenization lysates.

As used herein the phrase "polar extract" refers to a crude extract further purified by the use of a polar solvent. Polar solvents, such as acetonitrile, water or ammonia, are well known in the art and may be used to obtain isolated fractions. Polar solvents, composed of polar molecules, can dissolve ionic compounds or covalent compounds that ionize in polar extracts thus resulting in isolated fractions. The polar extracts of the present invention may comprise any percentage of polar solvent including for example 1-10% polar solvent, 10-20% polar solvent, 20-30% polar solvent, 30-40% polar solvent, 40-50% polar solvent, 50-60% polar solvent, 70-80% polar solvent, 80-90% polar solvent and 90-100% polar solvent.

According to one embodiment of this aspect of the present invention, the polar extract is derived from tentacle tissue or acrorhageal tissue of a sea anemone (e.g. *Actinia equine*). Exemplary polar extracts derived from *Actinia equine* may comprise about 1-10% acetonitrile, about 40-60% acetonitrile or about 70-90% acetonitrile, (v/v of total composition). Furthermore, the polar extract of the present invention may be from *Aiptasia pulchella*. The polar extract from *Aiptasia pulchella* may comprise about 8-12% acetonitrile, about 16-20% acetonitrile, about 22-26% acetonitrile or about 26-30% acetonitrile (v/v of total composition).

According to one embodiment, the active agents in the compositions of the present invention are polypeptides. For example, the present inventors have shown that active agents in the *Actinia equina* and the *Aiptasia pulchella* fractions were polypeptides (FIG. 7B for *Actinia equina* and data not shown for *Aiptasia pulchella*). A non-limiting example is SEQ ID NO:1. Thus, exemplary polypeptide agents that may serve as active agents in the compositions of the present invention are those characterized by a peak mass of 19863 Da, 9926 Da, 8261 Da or 3655 Da. A protein peak mass is measured by any instrument known to one of ordinary skill in the art, for example, by MS-analysis such as MALDI-TOF (Voyager-DE STR Applied Biosystems) using sinapinic acid as a matrix.

The compositions of the present invention may also be expressed in-vivo using genetic engineering techniques (e.g. using transgenic aquatic sessile organisms).

An exemplary polypeptide agent derived from an aquatic organism that may be used to prevent cell adhesion is equinatoxin. Equinatoxins (i.e., equinatoxins 1, 2 and 3) are well known in the art as pore forming toxins found in sea anemones (e.g., *Actinia equina*). Equinatoxins, may be comprised in sea anemone cells or may be isolated therefrom. Any equinatoxin may be used according to the teachings of the present invention for inhibiting cell adhesion to a surface.

According to another embodiment, the active agents in the compositions of the present invention are polysaccharides. For example, the present inventors have shown that active agents in the *Aiptasia pulchella* were polysaccharides (FIGS. 10-11A-C). Thus, exemplary polysaccharide agents that may serve as active agents in the compositions of the present invention are those characterized by size exclusion HPLC. Polysaccharide characterization can be effected by any method known to one of ordinary skill in the art, for example, by PACE (polysaccharide analysis using carbohydrate gel electrophoresis).

According to one embodiment of this aspect of the present invention, the compositions of the present invention are devoid of cytotoxic or cytostatic activity—e.g. they are not bactericidal or bacteristatic.

According to another embodiment of this aspect of the present invention, the activity of the active agent of the compositions of the present invention is preserved following lyophilization.

As indicated earlier, the compositions of the present invention may be used to prevent biofilm formation in vivo. Accordingly, the present invention contemplates pharmaceutical compositions that may be used to prevent or treat infections in the body.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein the term "active ingredient" refers to the aquatic organism compositions (and agents purified therefrom) accountable for the intended biological effect.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference and are further described herein below.

As mentioned, the pharmaceutical compositions of the present invention may be administered to a subject in need thereof in order to prevent or treat a pathogen infection.

As used herein the term "subject in need thereof" refers to a mammal, preferably a human subject.

As used herein the term "treating" refers to curing, reversing, attenuating, alleviating, minimizing, suppressing or halting the deleterious effects of a pathogen infection.

As used herein the phrase "pathogen infection" refers to any medical condition which is caused by a pathogenic organism. Examples of pathogen infections include, but are not limited to, chronic infectious diseases, subacute infectious diseases, acute infectious diseases, viral diseases, bacterial diseases, protozoan diseases, parasitic diseases, fungal diseases, mycoplasma diseases, archaea diseases and prion diseases.

According to one embodiment, the pathogen infection is caused by an organism capable of growing in or on a biofilm.

Examples of pathogen infections caused by microbial biofilms include native valve endocarditis (NVE), otitis media (OM), chronic bacterial prostatitis, cystic fibrosis (CF) and periodontitis. Additional pathogen infections that are not specifically attributed to biofilms include, but are not limited to urinary infections, female genital tract infections and pneumonia. Infections due to implantation of medical devices include vascular catheter infections, arterial prosthetic infections, infections of prosthetic heart valves, prosthetic joint infections, infections of central nervous system shunts, orthopedic implant infections, pacemaker and defibrillator infections, hemodialysis and peritoneal dialysis infections, ocular infections, urinary tract infections, infections of the female genital tract, infections associated with endotracheal intubation and tracheostomy and dental infections.

As used herein the phrase "pathogenic organism" refers to any single cell organism which is capable of causing disease, especially a living microorganism such as a bacteria or fungi. Preferably the pathogenic organism is capable of growing in or on a biofilm. Many common pathogenic organisms exist in mammals (e.g. humans) as biofilms and cause disease. These include, but are not limited to, *Mannheimia haemolytica* and *Pasteurella multocida* (causing pneumonia), *Fusobacterium necrophorum* (causing liver abscess), *Staphylococcus aureus* and *Pseudomonas aeruginosa* (causing wound infections), *Escherichia coli* and *Salmonella* spp (causing enteritis), *Staphylococcus aureus* and *Staphylococcus epidermidis* (causing OM), and *Streptococci* sp., *Staphylococci* sp., *Candida*, and *Aspergillus* sp. (causing NVE).

It will be appreciated that treatment of infectious diseases according to the present invention may be combined with other treatment methods known in the art (i.e., combination therapy). These include, but are not limited to, antimicrobial agents such as penicillins, cephalosporins, carbapenems, aminoglycosides, macrolides, lincomycins, tetracyclines, chloramphenicol, and griseofulvin.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For topical administration, the compositions of the present invention may be formulated as a gel, a cream, a wash, a rinse or a spray.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., an aquatic organism composition) effective to prevent, alleviate, or ameliorate symptoms of a pathogenic infection (e.g., fever) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

As mentioned, medical devices and implants are commonly infected with opportunistic bacteria and other infectious microorganisms (e.g., fungi) in some cases necessitating the removal of implantable devices. Such infections can also result in illness, long hospital stays, or even death. The prevention of biofilm formation and infection of medical devices is therefore highly desirous.

Thus, the present invention also contemplates medical devices in which the above-described compositions are attached thereto.

As used herein the term "medical device" refers to any implant, instrument, apparatus, implement, machine, device or any other similar or related object (including any component or accessory), which is intended for use in the diagnosis, treatment, cure or prevention of disease or other conditions. Such medical device is intended for use in man or other animals and is anticipated to affect the structure or any function of the body. Such medical device does not achieve its primary intended purposes through chemical action and is not dependent upon being metabolized for the achievement of its primary intended purposes.

As used herein the term "implant" refers to any object intended for placement in a human body that is not a living tissue. The implant may be temporary or permanent. An implant can be an article comprising artificial components, such as catheters or pacemakers. Implants can also include naturally derived objects that have been processed so that their living tissues have been devitalized. As an example, bone grafts that have been processed so that their living cells are removed (acellularized), but so that their shape is retained to serve as a template for ingrowth of bone from a host. As another example, naturally occurring coral can be processed to yield hydroxyapatite preparations that can be applied to the body for certain orthopedic and dental therapies.

The present invention therefore envisions coating medical devices with the compositions of the present invention to prevent cell adherence thereto so as to reduce/eliminate any possible cell aggregation and biofilm formation known to occur following implantation. Device-related infections usually result from the introduction of microorganisms, primarily bacteria, during the device insertion or implantation procedure, or from attachment of blood-borne organisms to the newly inserted device and their subsequent propagation on its surface. Coating the medical device with the compositions of the present invention will therefore inhibit biofilm formation of one or more microbial species, will prevent medical device related infections, and consequently will reduce the need of antibiotic treatment or removal of the medical device from the subject.

Medical devices that may be coated according to the teachings of the present invention include, but not limiting to, artificial blood vessels, catheters and other devices for the removal or delivery of fluids to patients, artificial hearts, artificial kidneys, orthopedic pins, prosthetic joints, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, mechanical heart valves, artificial joints, artificial larynxes, otological implants), anastomotic devices, vascular catheter ports, vascular stents, clamps, embolic devices, wound drain tubes, ocular lenses, dental implants, hydrocephalus shunts, pacemakers and implantable defibrillators, needleless connectors, voice prostheses and the like.

Another possible application of the aquatic organism compositions of the present invention is the coating of surfaces found in the medical and dental environment. Such surfaces include the inner and outer aspects of various instruments and devices, whether disposable or intended for repeated uses. Such surfaces include the entire spectrum of articles adapted for medical use, including without limitation, scalpels, needles, scissors and other devices used in invasive surgical, therapeutic or diagnostic procedures; blood filters. Other examples will be readily apparent to practitioners in these arts.

Surfaces found in the medical environment also include the inner and outer aspects of pieces of medical equipment, medical gear worn or carried by personnel in the health care setting. Such surfaces can include surfaces intended as biological barriers to infectious organisms in medical settings, such as gloves, aprons and faceshields. Commonly used materials for biological barriers are thermoplastic or polymeric materials such as polyethylene, dacron, nylon, polyesters, polytetrafluoroethylene, polyurethane, latex, silicone and vinyl. Other surfaces can include counter tops and fixtures in areas used for medical procedures or for preparing medical apparatus, tubes and canisters used in respiratory treatments, including the administration of oxygen, of solubilized drugs in nebulizers and of anesthetic agents. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

The aquatic organism compositions of the present invention can be used on the surface of or within these medical devices to provide long term protection against microorganism colonization and reduce the incidence of device-related infections. These compositions can also be incorporated in combination with an anti-microbial agent (e.g., antibiotic agent) into coatings for medical devices. Such a combination will sufficiently kill or inhibit the initial colonizing bacteria and prevent device-related infections as long as the substance is presented in an inhibitory concentration at the device-microbe interface.

The aquatic compositions of the present invention can be directly incorporated into the polymeric matrix of the medical device at the polymer synthesis stage or at the device manufacture stage. The aquatic compositions can also be covalently attached to the medical device polymer. These and many other methods of coating medical devices are evident to one of ordinary skill in the art.

Additional surfaces that can be treated according to the teachings of the present invention include the inner and outer aspects of those articles involved in water purification, water storage and water delivery, and those articles involved in food processing. Thus the present invention envisions coating a solid surface of a food or beverage container to extend the shelf life of its contents.

Surfaces related to health can also include the inner and outer aspects of those household articles involved in providing for nutrition, sanitation or disease prevention. Thus, the aquatic compositions of the present invention can be used for removal of disease-causing microorganisms from external surfaces. These can include, for example food processing equipment for home use, materials for infant care, tampons, soap, detergents, health and skincare products, household cleaners and toilet bowls.

The surface may be also be laboratory articles including, but not limited to, microscopic slide, a culturing hood, a Petri dish or any other suitable type of tissue culture vessel or container known in the art.

The inventors of this application also envision the use of the aquatic organism compositions of the present invention as anti-fouling agents.

As used herein the term "anti-fouling agents" refers to the compounds used to protect underwater surfaces from attaching single cell organisms. These single cell organisms include microorganism such as bacteria and fungi.

These underwater surfaces include any water immersed surface, including ships'/boats's hulls (i.e., the body or frame of a ship or boat), submergence vehicles, navigational aids, screens, nets, constructions, floating or emplaced off-shore platforms (e.g., docks), buoys, signaling equipment and articles which come into contact with sea water or salty water. Other underwater surfaces include structures exposed to sea water including pilings, marine markers, undersea conveyances like cabling and pipes, fishing nets, bulkheads, cooling towers, and any device or structure that operates submerged.

The aquatic organism compositions of the present invention can be incorporated into marine coatings to limit undesirable marine fouling. Thus, the anti-fouling agents of the present invention can be formulated so as not to contain toxic materials (such as heavy metals), and still retain their efficacy. The anti-fouling paint of the present invention may further, contain binders(s), pigment(s), solvent(s) and additive(s).

Examples of solvents that may be used include aromatic hydrocarbons such as xylene and toluene; aliphatic hydrocarbons such as hexane and heptane, esters such as ethyl acetate and butyl acetate; amides such as N-methylpyrrolidone and N,N-dimethylformamide; alcohols such as isopropyl alcohol and butyl alcohol; ethers such as dioxane, THF and diethyl ether; and ketones such as methyl ethyl ketone, methyl isobutyl ketone and methyl isoamyl ketone. The solvents may be used alone or in combination thereof.

Examples of binders that may be used include alkyd resin, acrylic or vinyl emulsions, polyurethane resins, epoxy resins, silicone based resins, acrylic resins, inorganic silicate based resins, vinyl resins, particularly a vinyl chloride/vinyl acetate copolymer, and rosin.

Examples of pigments that may be used include titanium dioxide, cuprous oxide, iron oxide, talc, aluminium flakes, mica flakes, ferric oxide, cuprous thiocyanate, zinc oxide, cupric acetate meta-arsenate, zinc chromate, zinc dimethyl dithiocarbamate, zinc ethylene bis(dithiocarbamate) and zinc diethyl dithiocarbamate.

Examples of additives that may be incorporated into the coating composition include dehumidifiers, wetting/dispersing agents, anti-settling agents, anti-skinning agents, drying/curing agents, anti-marring agents and additives ordinarily employed in coating compositions as stabilizers and anti-foaming agents. Additionally, any antibiotic which is relatively insoluble in seawater can be used with an anti-fouling marine paint.

Methods of preparing marine anti-fouling paints are explained in detail in U.S. Pat. No. 4,678,512; U.S. Pat. No. 4,286,988; U.S. Pat. No. 4,675,051; U.S. Pat. No. 4,865,909; and U.S. Pat. No. 5,143,545.

It will be appreciated that the present invention has a variety of applications including identifying an agent comprising an anti-biofilm activity.

Thus, according to another aspect of the present invention, there is provided a method of identifying an anti-biofilm composition, comprising contacting a plurality of compositions from an aquatic organism with biofilm forming bacteria; assaying a biofilm activity of the biofilm forming bacteria in a presence of the plurality of compositions; and identifying from the plurality of compositions at least one composition having the anti-biofilm activity above a predetermined threshold, thereby identifying the anti biofilm composition.

As used herein the phrase "biofilm forming bacteria" refers to any bacteria which can form and/or live in a biofilm. Such bacteria include gram positive and gram negative bacteria, as further described herein above.

As shown by the present inventors (Example 3), assaying the biofilm activity of biofilm forming bacteria may be accomplished by bacterial adhesion bioassays. Any bacterial adhesion bioassay know in the art can be used. Examples of such methods include high-throughput polystyrene microplate assays, qualitative bacteria adhesion assay or fluorescent microscopic assays for biofilm formation on glass slides.

As used herein the phrase "predetermined threshold" refers to the threshold of the number of bacteria adhering to a surface. Preferably, the anti-biofilm composition is able to decrease biofilm formation by as much as 10%, more preferably by 20%, more preferably by 30%, more preferably by 40%, more preferably by 50%, more preferably by 60%, more preferably by 70%, more preferably by 80%, more preferably by 90% and most preferably by 100%.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752;. 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Fish and *Cnidarians* Crude Extracts Act in an Anti-Adhesive Manner

Materials and Other Experimental Organisms

*Cnidarians* and Other Experimental Organisms

*Cnidarians* and other experimental organisms including the sea anemones *Actinia equina* and *Aiptasia pulchella* as well hydroids *Chlorohydra viridissima* and *Hydra vulgaris* were grown and maintained in the laboratory or collected directly from their natural habitat.

Sample Collection

Samples were collected from surface mucous of fish (eel, catfish) and homogenates of sessile *cnidarians* (from two kinds of hydrae and sea anemones). Briefly, 300 mg wet weight of anemone tissue were dissected, rinsed in distilled water (DDW), homogenized in a volume of 300 µl DDW (total volume of about 500 µl), centrifuged (3 min, 14000×g) and prefiltered (0.2 µl).

Bacteria Growth

All bacteria strains were grown in triplicates for individual experiments. *Acinetobacter baumanni, Staphylococcus aureus, Pseudomonas aurigenose* were grown in Trypto casein Soya Broth (TSB)+0.25% D-Glucose and *E. coli* strain U85 expressing GFP were grown in Luria-Bertani (LB) with 50 µg/ml Kanamycin.

Bacterial Adherence Bioassay

Biofilms were grown in 96-well round-bottom polystyrene plates. Samples collected as described above, were diluted in PBS and incubated with the virulent clinical bacterial strain *Acinetobacter baumannii*.

Briefly, 180 µl of *A. baumannii* cultures grown overnight were supplemented with 20 µl of appropriate samples (diluted in PBS). Following 24 hours of incubation at 37° C., wells were washed with water and stained with 250 µl crystal violet solution. The dye was removed by thorough washing with water. For quantification of attached cells, crystal violet was solubilized in 250 µl of 1% SDS and the absorbance was measured at 595 nm.

Results

Figure 1A:
FIGS. 1A-B are pictures depicting the sea anemone *Actinia equina*.
Figure 1B:
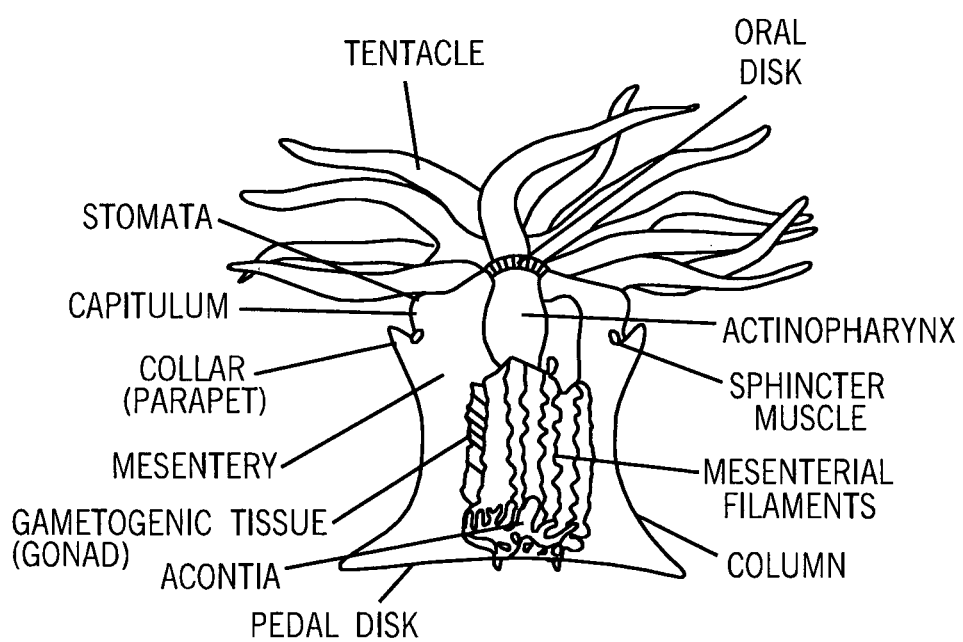

Crude extracts derived from body homogenates, samples of surface mucous collected from fish (eel, catfish) and sessile *cnidarians* (two kinds of hydrae and sea anemones) revealed a basic ability to prevent the adherence of virulent clinical isolates of the bacteria *Acinetobacter baumannii*. As is clear from FIG. 2, the highest efficacy was revealed by the extract of the sea anemone *Actinia equina* (illustrated in FIGS. 1A-B) tentacles.

Example 2

*Actinia equina* Extracts Function as an Anti-Adhesive But Are Not Bacteriocidal Materials and Experimental Procedures

*Actinia equina*

The sea anemone *Actinia equina* was grown and maintained in the laboratory.

Sample Collection

Homogenates of sessile cnidarians (*Actinia equina*) was collected. Briefly, 300 mg wet weight of anemone tissue were dissected, rinsed in distilled water, homogenized in a volume of 300 µl DDW (total volume of about 500 µl), centrifuged (3 min, 14000×g) and prefiltered (0.2 µl).

Column Chromatography and Protein Chemistry

Samples (100 µl) were separated on an analytical C8 (Thermo-Hypersil, Keystone) or C-18 (Vydac) column, eluted by a linear gradient of acetonitrile in DDW+0.1% Trifluoroacetic acid (TFA, 3-80% from 5 to 75 minutes). The elution pattern was monitored at 215 nm.

Bacteria Growth

As described in Example 1.

Bacterial Adherence Bioassay

As described in Example 1.

Bacterial Killing/Growth Inhibition

Figure 4:
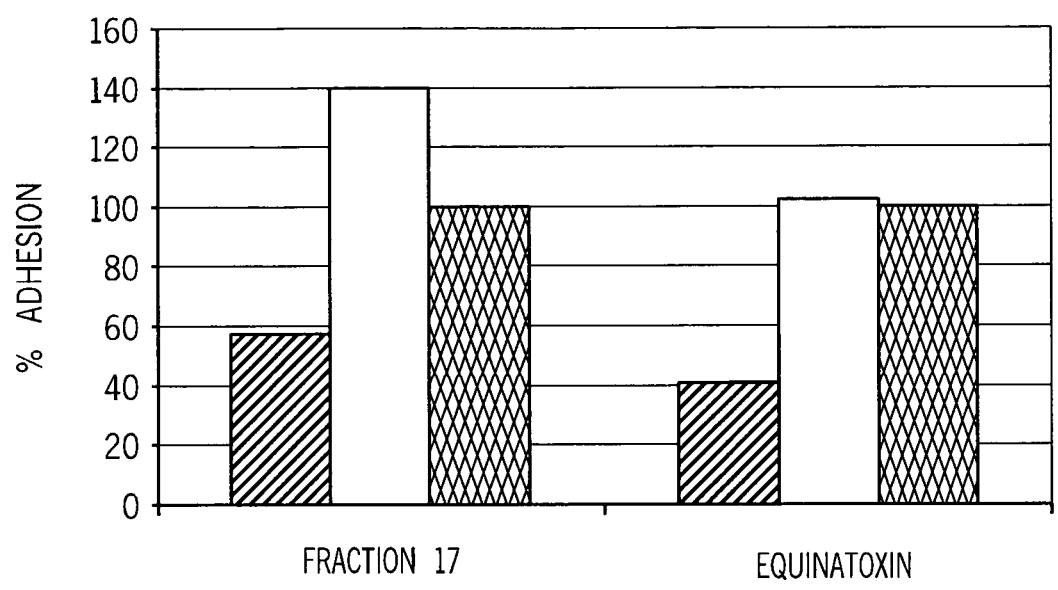
FIG. 4 is a bar graph depicting heat lability of anti-adhesive activity. The adherence of *A. Baumannii* to a polystyrene microplate was assayed with the addition of fraction 17 from the tentacle separation or with recombinant equinatoxin, both with and without heat inactivation. Both compounds were tested at 1:100 dilutions and results are shown as percent adherence relative to control PBS (100%). p

Crude extract of *A. equine* tentacles, as well as isolated fractions (see FIG. 4 below), were added to a liquid culture of the bacteria *A. baumanni*. Overnight growth of bacteria was recorded by measurement of the optical density of the cultures at 600 nm.

Protein Gel Electrophoresis

100 µl of the active fractions were precipitated with ice-cold acetone, resuspended in running buffer containing SDS and β-mercapthoethanol, boiled for 3 minutes and separated on a 15% denaturing SDS-PAGE gel. Following electrophoresis the gel was silver stained.

Heat Denaturation of Samples

Heat denaturation was carried out by subjecting sample to 100° C. for 30 min in a PCR thermocycle.

Results

Figure 3A:
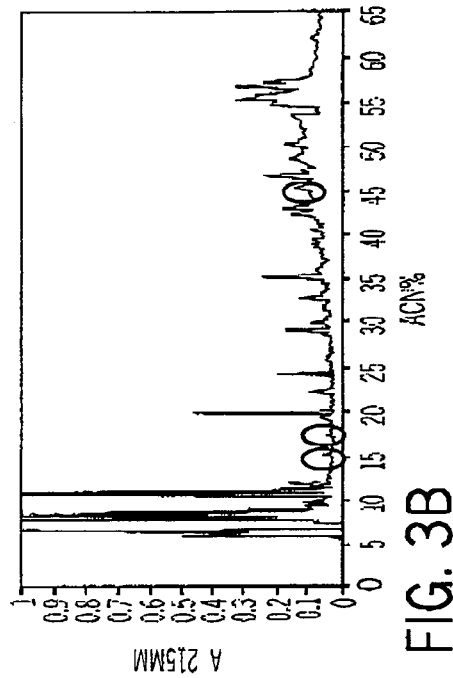
FIGS. 3A-D are graphs depicting chromatographic separation and characterization of anti-adhesive fractions from *Actinia equine*.
Figure 3B:
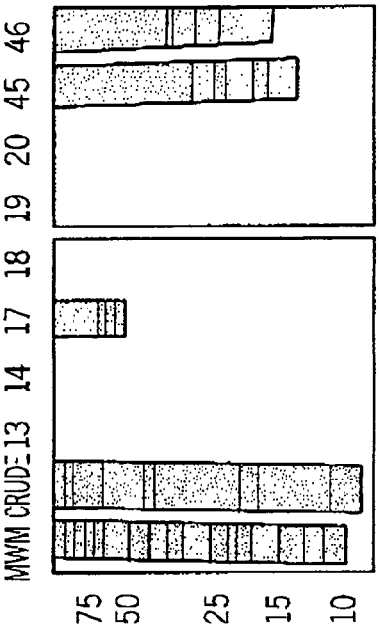
Figure 3C:
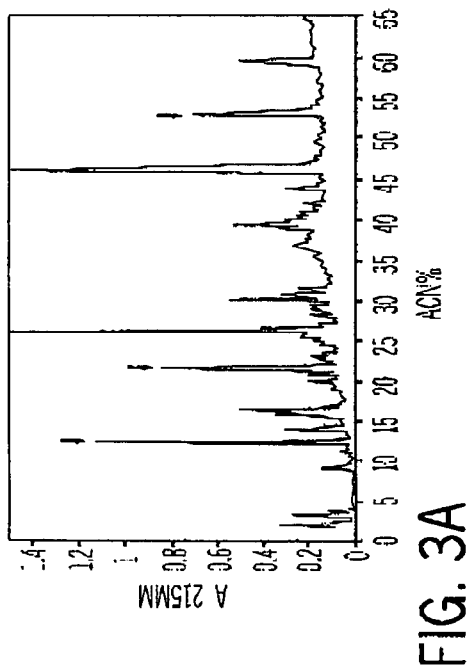
Figure 3D:
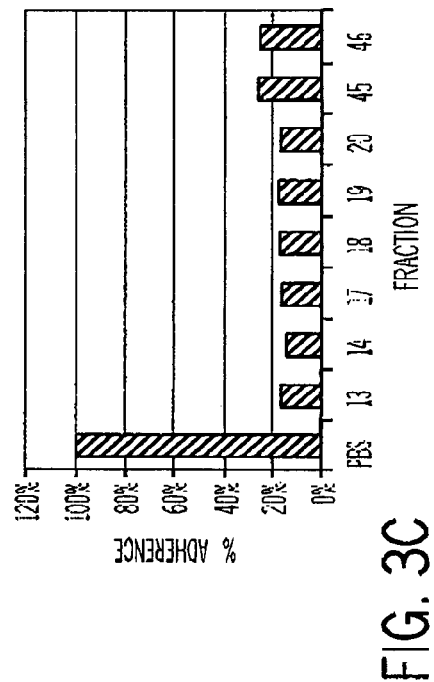

A bacterial anti-adhesion effect on *Acinetobacter baumannii* was revealed by fractions obtained from the chromatographic separation of *Actinia acrorhageal* tissue (FIG. 3A) and *Actinia tentacular* tissue (FIG. 3B). It is noteworthy that the separations were performed on analytical reversed phase (RP) columns in an HPLC system, in the presence of an organic solvent, which demands lyophilization (for removal). This indicated that the active fractions obtained are stable and resist organic solvents and lyophilizations. In addition, FIG. 3D provides a rough indication (presented in an electrophoregrams) of the molecular masses of the active components and the degree of their homogeneity.

It is noteworthy that the adherence bioassay monitors bacterial adhesion to artificial surfaces. It does not represent bacterial killing or even bacterial growth inhibition. Furthermore, the avoidance (absence of killing or growth inhibition) was verified by a complementary measurement of OD 600 nm (measured particle density) of the treated versus control measurement after 24 hours of incubation with the extracts. Results (presented in Table 1, herein below) indicate that none of the anti-adhesion substances, crude extract of *Actinia equina* tentacles as well as isolated fractions (FIGS. 2 and 3A-D), revealed a bactericidal or growth inhibitory effect on *Acinetobacter baumannii* compared to bacteria grown in the presence of PBS (positive control).

TABLE 1

| Fraction | OD600 nm Time-0 | OD600 nm Time-24 hours |
|---|---|---|
| 13 | 0.342 | 1.142 |
| 14 | 0.342 | 1.287 |
| 17 | 0.342 | 1.012 |
| 18 | 0.342 | 1.108 |

TABLE 1-continued

| Fraction | OD600 nm Time-0 | OD600 nm Time-24 hours |
|---|---|---|
| 19 | 0.342 | 1.180 |
| 20 | 0.342 | 1.362 |
| 45 | 0.342 | 1.089 |
| 46 | 0.342 | 1.302 |
| Actinia tentacle Crude | 0.342 | 1.054 |
| Positive control | 0.342 | 1.210 |

The tentacular fraction 17 and equinatoxin, a pore forming peptide that exhibits anti-biofilm and anti-adherence activity on broad spectrum of microbes (FIG. 4), as well as fractions 13, 14, crude extract and acrorhageal fractions (data not shown) were shown to lose their bacterial anti-adhesion activity following heat denaturation and by treatment with proteinase K (data not shown). Taken together this information suggests that the active factors are polypeptides.

The anti-adherence effect of tentacular fractions was further demonstrated on four different groups of bacteria namely *Acinetobacter baumannii*, *Pseudomonas aeruginosa*, *Escherichia coli* (all Gram-negative bacteria belonging to different families of bacteria) and *Staphylococcus aureus* (Gram-positive bacteria). While *E. coli* belongs to the Enterobacteriaceae which live in the intestinal tracts of animals, *P. aeruginosa* and *A. baumannii* are free-living organisms in soil and water which belong to the order Pseudomonadales but differ in their family. As evident from FIG. 5, tentacular fraction 13 exhibited an anti-adherence effect on all four groups of bacteria.

Example 3

*Actinia equine* Crude Extract Effects Initial Stages of Biofilm Formation

Materials and Experimental Procedures

*Actinia equina*

The sea anemone *Actinia equina* was grown and maintained in the laboratory.

Sample Collection

Homogenates of sessile cnidarians (*Actinia equina*) was collected. Briefly, 300 mg wet weight of anemone tissue were dissected, rinsed in distilled water, homogenized in a volume of 300 µl DDW (total volume of about 500 µl), centrifuged (3 min, 14000×g) and prefiltered (0.2 µl).

Bacteria Growth

As described in Example 1.

A High-Throughput Polystyrene Microplate Assay

Various bacteria (e.g., *S. aureus* ATCC 25923) were grown in 96-well round-bottom polystyrene plates. After 24 hours of incubation at 37° C., each well was washed with water and stained with 250 µl crystal violet solution. The dye was removed by thorough washing with water. For quantification of attached cells, crystal violet left in the wells was solubilized in 250 µl of 1% SDS, and the optical density read at 595 nm. Crude material of *A. equina* tentacles was added to the plates at time 0 at 3 dilutions 1:10, 1:100 and 1:1000, in triplicates. Bacteria were incubated with PBS alone as positive control.

Qualitative Bacteria Adhesion Assay

*S. aureus* ATCC 25923 were grown in 2 ml medium in 5 ml polystyrene tubes. After 24 hours of incubation at 37° C., each tube was washed with water and stained with 250 µl crystal violet solution. The dye was removed by thorough washing with water. For quantification of attached cells, crystal violet left in the wells was solubilized in 250 μl of 1% SDS; and the optical density read at 595 nm. Crude material of *A. equina* tentacles was added to the plates at time 0 at 3 dilutions 1:10, 1:100 and 1:1000, in triplicates. As positive control bacteria was incubated with PBS alone.

A Fluorescent Microscopic Assay for Biofilm Formation on Glass Slides

*E. coli* DH5-α strain U85 containing a plasmid for the expression of Green Fluorescent Protein (GFP) were incubated in 2 ml LB medium with glass cover slides and adhered bacteria were visualized with inverted epi-flouresent IX2-81 microscope (Olympus, USA). Crude material and fractions where added at time 0 and biofilm formation where checked after 1 hour, 7 hours and 22 hours.

Results

Figure 6A:
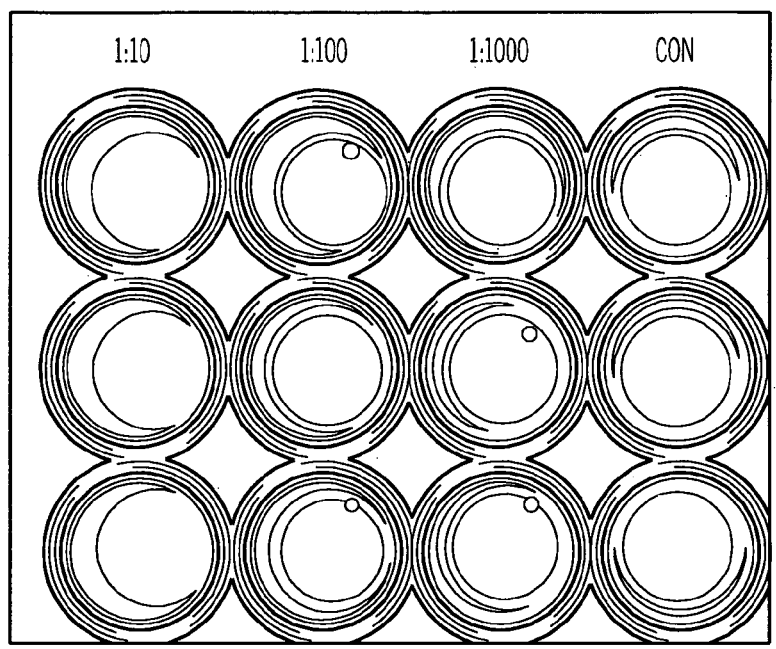
FIGS. 6A-C are three complementary assays for bacterial adhesion.
Figure 6B:
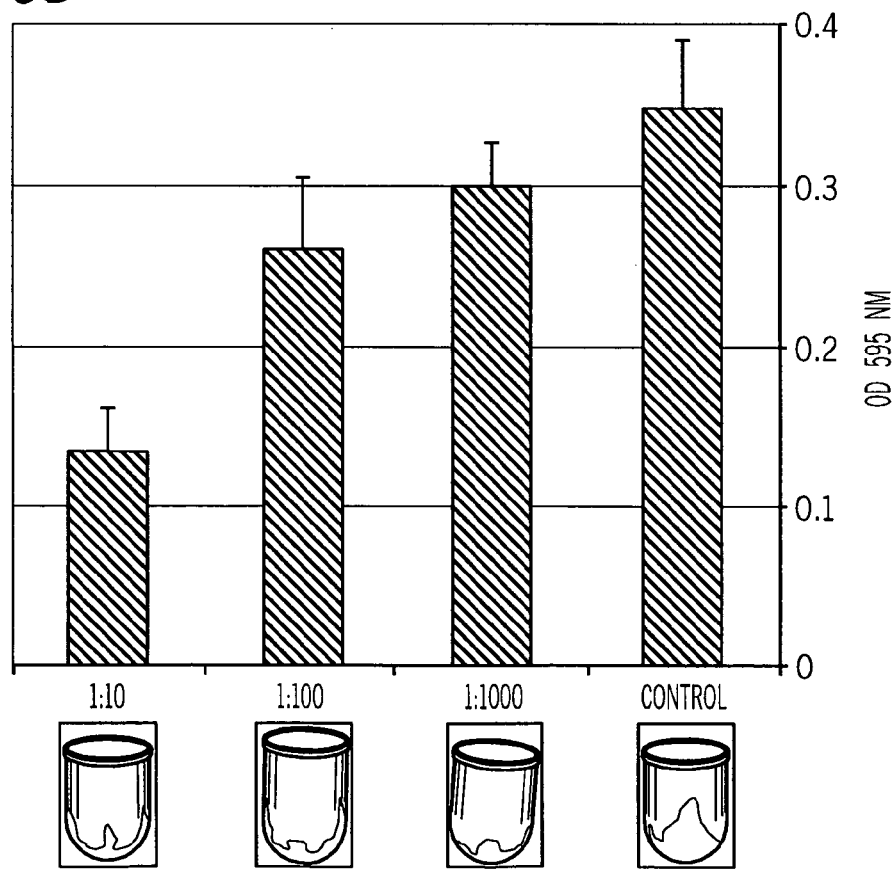
Figure 6C:
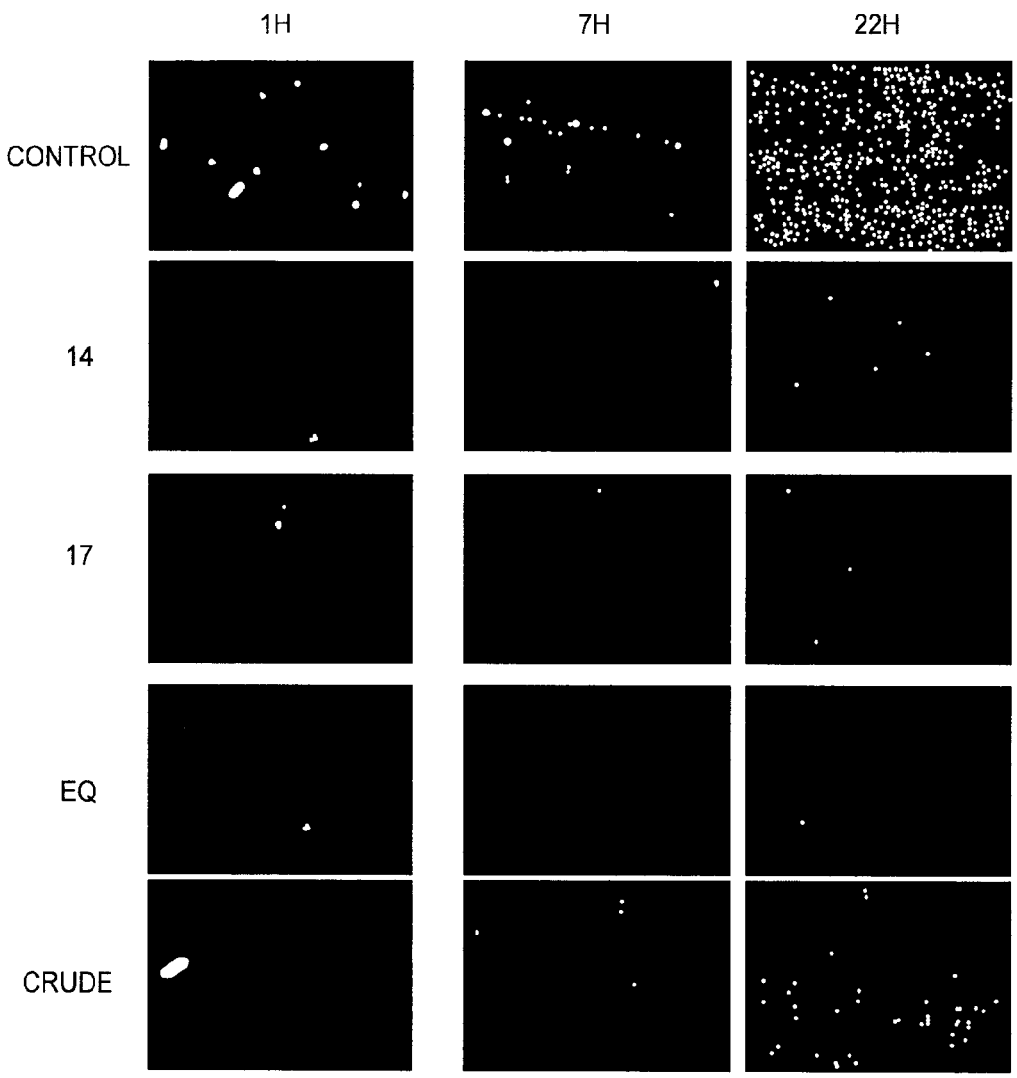

A decrease in attached bacteria is apparent due to the addition of *A. equina* tentacles crude material to the biofilm formation (FIGS. 6A and 6B). Moreover, as presented in FIG. 6C, bacterial adhesion is clearly seen already one hour following incubation with PBS, with a dense mat of bacteria observed after 22 hours. In contrast, incubation of the bacteria with *A. equina* tentacle extract, with two chromatographic fractions (14, 17) from this extract or with recombinant equinatoxin, resulted in an ablation of bacterial adherence. Thus, these results indicate that prevention of biofilm formation occurs at the initial stages of the attachment.

Example 4

*Actinia equine* Active Material can be Isolated

Materials and Experimental Procedures

*Actinia equina* The sea anemone *Actinia equina* was grown and maintained in the laboratory.

Sample Collection

Homogenates of sessile cnidarians (*Actinia equina*) was collected. Briefly, 300 mg wet weight of anemone tissue were dissected, rinsed in distilled water, homogenized in a volume of 300 μl DDW (total volume of about 500 μl), centrifuged (3 min, 14000×g) and prefiltered (0.2 μl).

Column Chromatography and Protein Chemistry

As described in Example 2.

Selection of Active Peaks and MS Analysis

Active material previously obtained by RP-HPLC (T-18) was rechromatographed on the same column and peaks were collected, lyophilized and dissolved in a standard volume of PBS. Volumes of 20 μl were assayed for bacterial anti-adhesive activity.

Additionally, lyophilized samples (active peak 75) were dissolved in 50% methanol-0.5% formic acid and measured by MALDI-TOF (Voyager-DE STR Applied Biosystems) using sinapinic acid as a matrix. The measurement was performed in the positive linear mode.

Bacteria Growth

As described in Example 1.

Bacterial Adherence Bioassay

As described in Example 1.

Results

Figure 7A:
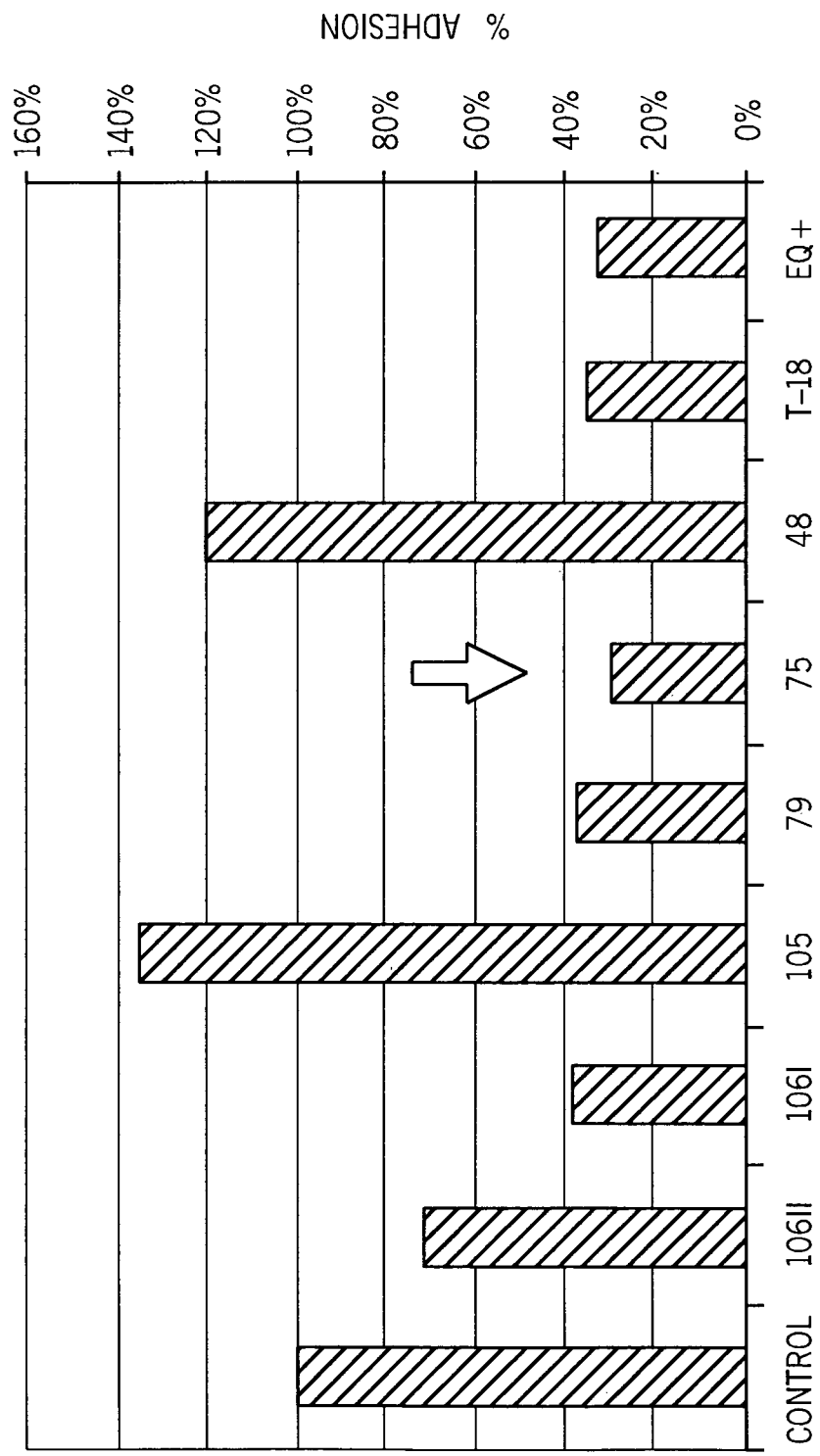
FIGS. 7A-B are graphs depicting selection of active peaks and MS analysis.
Figure 7B:
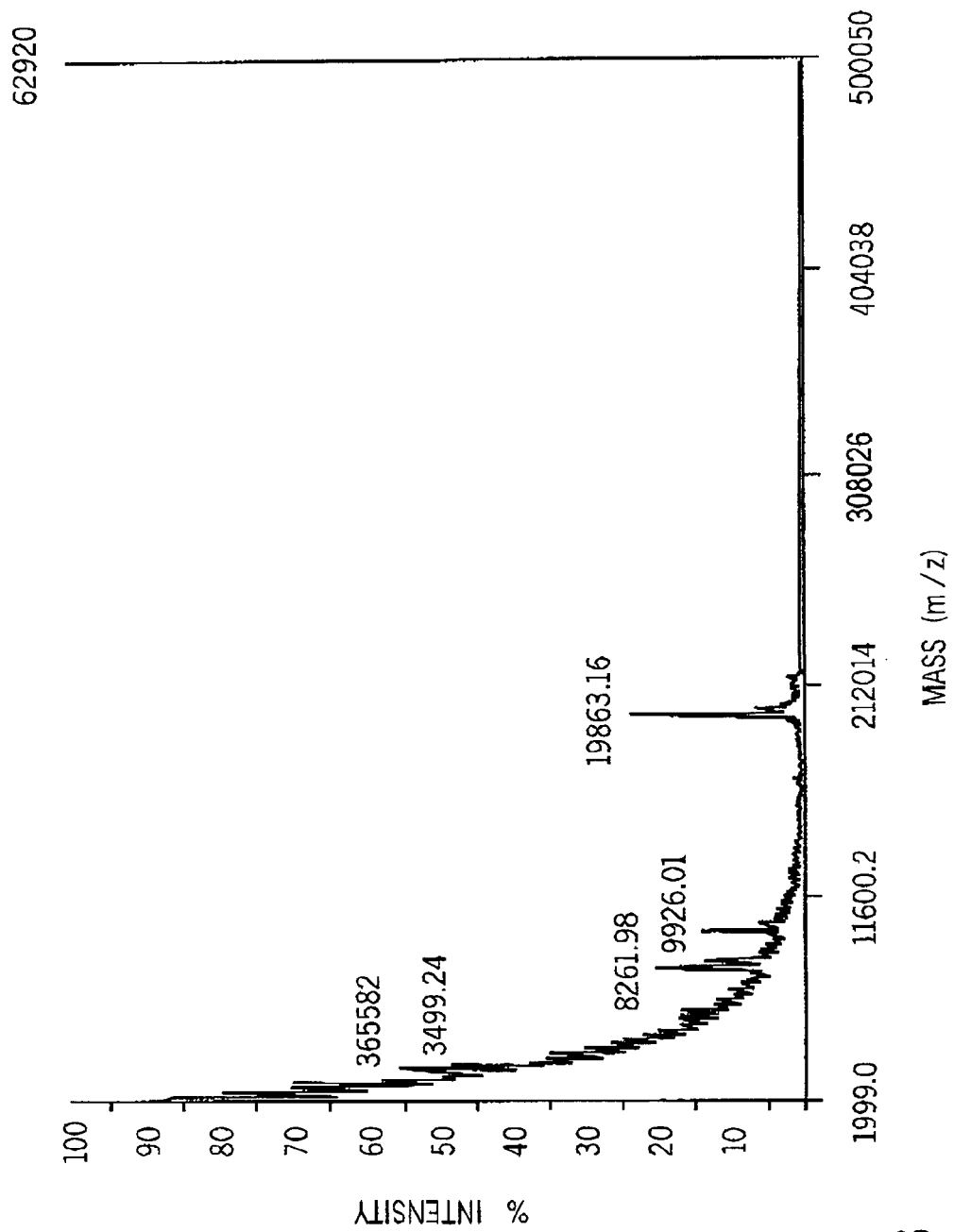

Rechromatographed active fraction T-18 (FIG. 7A) gave active fractions 75, 79 and 106I (FIG. 7A). MS analysis of fraction 75 (marked by red arrow) demonstrated several peaks at masses of 19863, 9926, 8261 and 3655 Da, presumably proteins (FIG. 7B). These data reveal the ability to isolate and chemically characterize the relevant substances.

Example 5

*Aiptasia pulchella* Extract Comprises Anti-Adhesive Activity

Materials and Experimental Procedures

Separation of Crude Material from *Aiptasia pulchella*

Separation of active fraction from *Aiptasia pulchella* was established using G-10 and G-75 gel filtration columns (GE Healthcare, Sweden). RP-HPLC with C-18 column of collected material from the gel filtration separations gave high resolution separation. Active fractions were analyzed by MS.

The high molecular fraction was rechromatographed on Sephadex G-75 and resulted in 2 fractions, both exhibited anti adherence/biofilm formation activity. Each of the resulted fractions was separated using RP-HPLC with c-18 column. This separation resulted in several fractions.

Results

Figure 8:
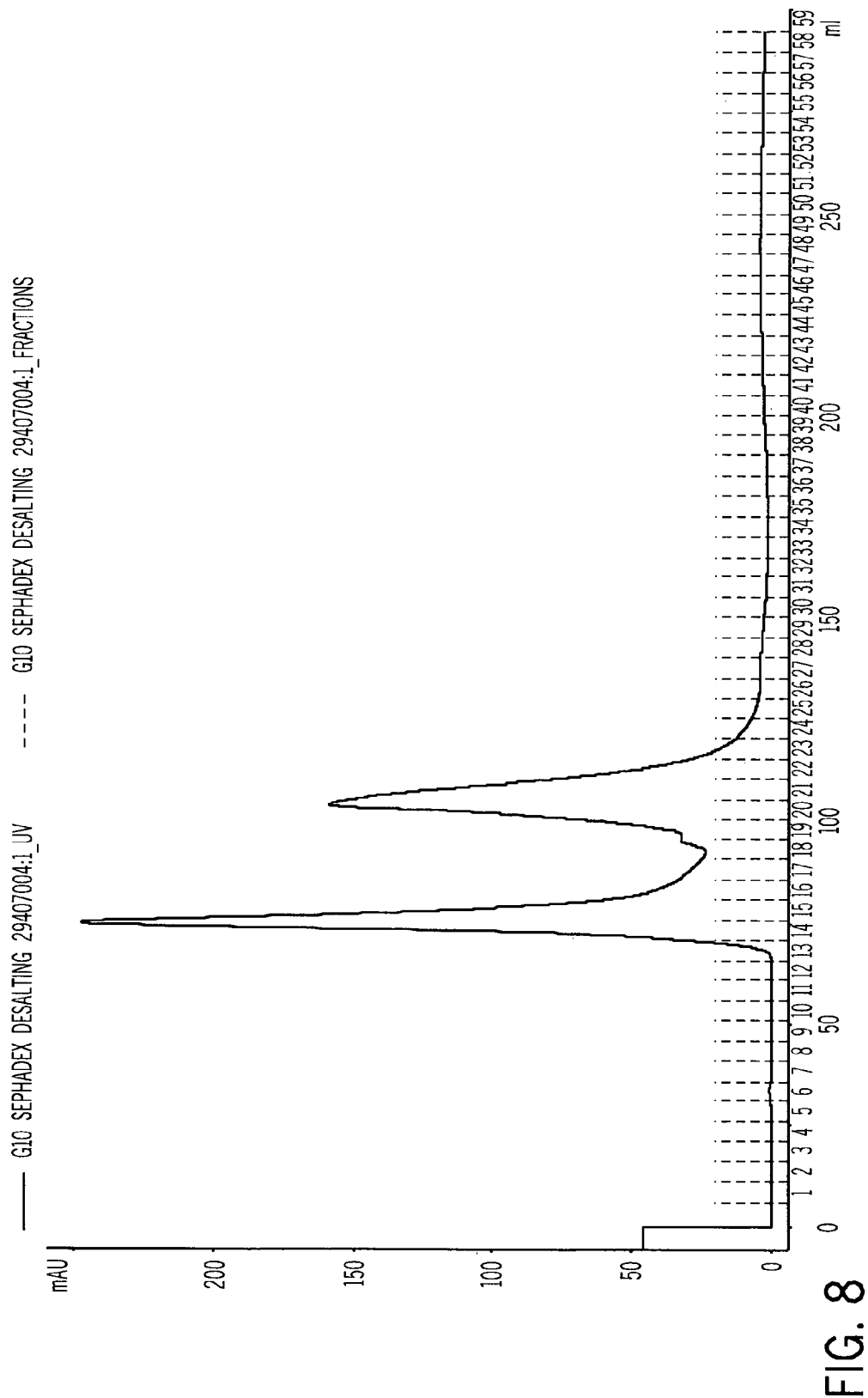
FIG. 8 is a graph depicting separation of *Aiptasia pulchella* crude extract. Figure shows chromatography of the crude extract on Sephadex G-10 resulting in 2 fractions, both exhibiting anti-adherence/biofilm formation activity.

Crude extract of *Aiptasia pulchella* (whole organism) separated on Sephadex G-10 column resulted in 2 fractions both exhibiting anti-adherence/biofilm formation activity (FIG. 8).

Figure 9:
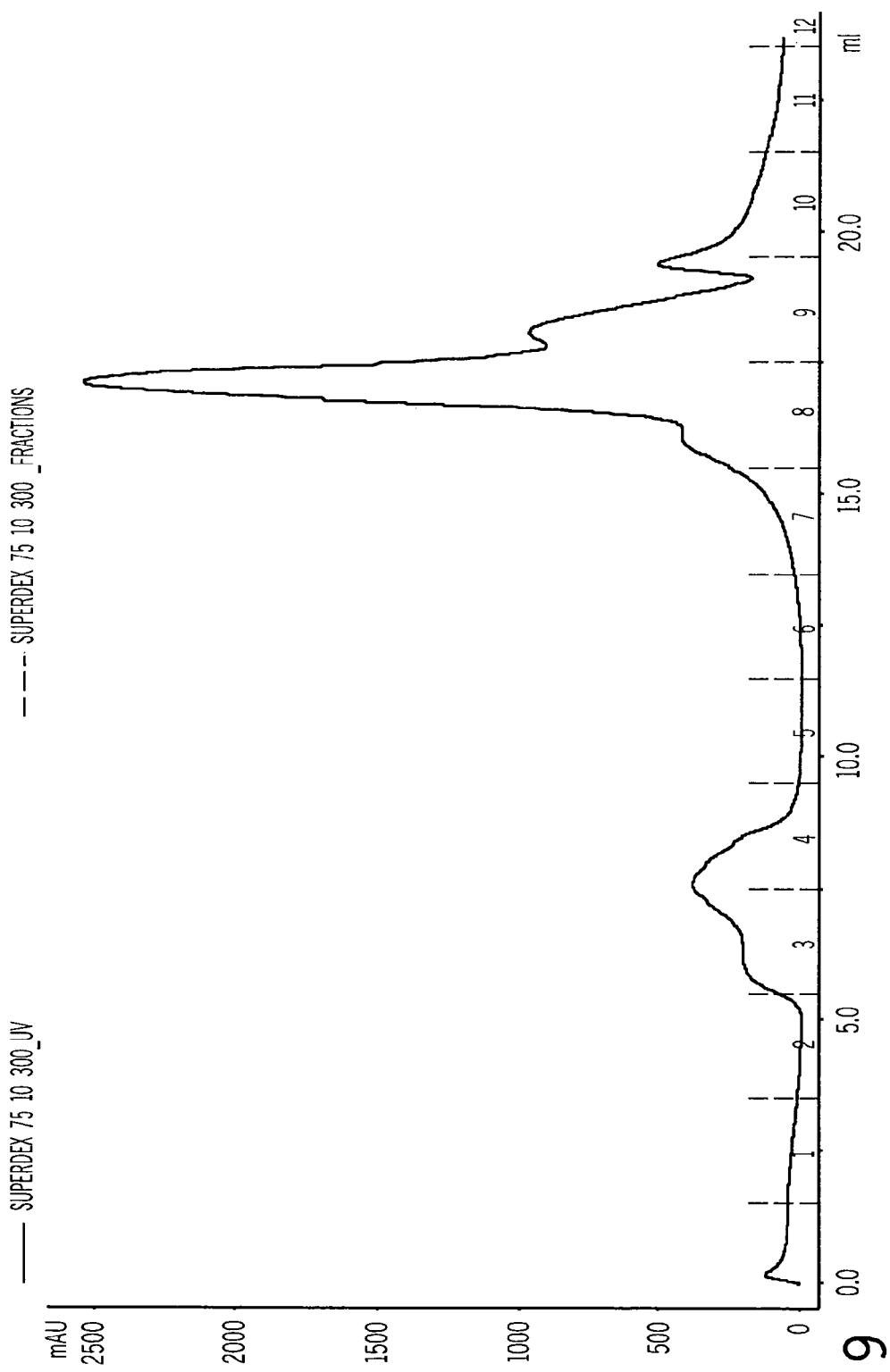
FIG. 9 is a graph depicting rechromatography of the high molecular fraction from Sephadex G-10 on Sephadex G-75, results in two main peaks represent high and low molecular fractions.

Rechromatography of the high molecular fraction from Sephadex G-10 on Sephadex G-75, resulted in two main peaks representing high and low molecular fractions (FIG. 9).

RP-HPLC separation with c-18 column of the low molecular fraction from the G-75 column resulted in several fractions including the active fractions (fractions 2 and 3, FIG. 10) which were identified as polysaccharides subsequent to HPLC analysis (FIGS. 11A-C). HPLC analysis of fractions 2 and 3 disclosed different combinations of monosugars for each fraction (FIGS. 11A-B). However, the main peak in both fraction 2 and fraction 3 (peak number 1) represents a di-glucose which makes up 45.5% of the total glycans of fraction 2 and approximately 91% of the total glycans of fraction 3 (Table 2).

TABLE 2

Distribution of Glycans

| | | % of total glycans | |
|---|---|---|---|
| Peak number | Amount of monosugars (estimate) | Fraction 2 (Z10FKR-2) | Fraction 3 ( Z10FKR-3) |
| 1 | 2 | 45.5 | 90.9 |
| 2 | 7 | 2.0 | — |
| 3 | 8 | 1.6 | — |
| 4 | 9 | 21.9 | 0.3 |
| 5 | 10 | 19.7 | 0.5 |
| 6 | 11 | 9.5 | 2.5 |
| 7 | 12 | — | 5.7 |

RP-HPLC separation with C-18 column of the high molecular fraction from G-75 gave at least 3 fractions (13, 18 and 20, FIG. 12) with high anti-adherence activity. MS analysis and gel electrophoresis showed that the active fractions are peptides (data not shown)

Sequence listing:

SEQ ID NO: 1:
MSRLIIVFIVVTMICSATALPSKKIIDEDEEDEKRSADVAGAVIDGASLS

```
FDILKTVLEALGNVKRKIAVGVDNESGKTWTALNTYFRSGTSDIVLPHKV

PHGKALLYNGQKDRGPVATGAVGVLAYLMSDGNTLAVLFSVPYDYNWYSN

WWNVRIYKGKRRADQRMYEELYYNLSPFRGDNGWHTRNLGYGLKSRGFMN

SSGHAILEIHVSKA
```

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A method of inhibiting or reducing adhesion of bacteria to a surface comprising administering an effective amount of an isolated and purified protein obtained from Actinia equina, wherein the protein has a molecular weight of around 60 KDa and the sequence of SEQ ID:1, to said surface.

* * * * *

SEQUENCE LISTING

```
<160> NUMBER OF SEQ ID NOS: 1

<210> SEQ ID NO 1
<211> LENGTH: 214
<212> TYPE: PRT
<213> ORGANISM: Actinia equina

<400> SEQUENCE: 1

Met Ser Arg Leu Ile Ile Val Phe Ile Val Thr Met Ile Cys Ser
1               5                   10                  15

Ala Thr Ala Leu Pro Ser Lys Lys Ile Ile Asp Glu Asp Glu Asp
                20                  25                  30

Glu Lys Arg Ser Ala Asp Val Ala Gly Ala Val Ile Asp Gly Ala Ser
                35                  40                  45

Leu Ser Phe Asp Ile Leu Lys Thr Val Leu Glu Ala Leu Gly Asn Val
                50                  55                  60

Lys Arg Lys Ile Ala Val Gly Val Asp Asn Glu Ser Gly Lys Thr Trp
65                  70                  75                  80

Thr Ala Leu Asn Thr Tyr Phe Arg Ser Gly Thr Ser Asp Ile Val Leu
                85                  90                  95

Pro His Lys Val Pro His Gly Lys Ala Leu Leu Tyr Asn Gly Gln Lys
                100                 105                 110

Asp Arg Gly Pro Val Ala Thr Gly Ala Val Gly Val Leu Ala Tyr Leu
                115                 120                 125

Met Ser Asp Gly Asn Thr Leu Ala Val Leu Phe Ser Val Pro Tyr Asp
130                 135                 140

Tyr Asn Trp Tyr Ser Asn Trp Trp Asn Val Arg Ile Tyr Lys Gly Lys
145                 150                 155                 160

Arg Arg Ala Asp Gln Arg Met Tyr Glu Glu Leu Tyr Tyr Asn Leu Ser
                165                 170                 175

Pro Phe Arg Gly Asp Asn Gly Trp His Thr Arg Asn Leu Gly Tyr Gly
                180                 185                 190

Leu Lys Ser Arg Gly Phe Met Asn Ser Ser Gly His Ala Ile Leu Glu
                195                 200                 205

Ile His Val Ser Lys Ala
210
```